US012702700B2

(12) United States Patent
Wu et al.

(10) Patent No.: US 12,702,700 B2
(45) Date of Patent: Aug. 11, 2026

(54) LACTATE RESPONSE SYSTEM AND METHODS

(71) Applicant: The University of Chicago, Chicago, IL (US)

(72) Inventors: Xiaoyang Wu, Chicago, IL (US); Jian Zhang, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1282 days.

(21) Appl. No.: 17/595,326

(22) PCT Filed: May 15, 2020

(86) PCT No.: PCT/US2020/070052
§ 371 (c)(1),
(2) Date: Nov. 15, 2021

(87) PCT Pub. No.: WO2020/232474
PCT Pub. Date: Nov. 19, 2020

(65) Prior Publication Data

US 2022/0211822 A1 Jul. 7, 2022

Related U.S. Application Data

(60) Provisional application No. 62/848,432, filed on May 15, 2019.

(51) Int. Cl.

| | |
|---|---|
| ***A61K 38/47*** | (2006.01) |
| ***A61K 9/06*** | (2006.01) |
| ***A61K 38/16*** | (2006.01) |
| ***A61K 47/32*** | (2006.01) |

(52) U.S. Cl.
CPC ................ *A61K 38/47* (2013.01); *A61K 9/06* (2013.01); *A61K 38/164* (2013.01); *A61K 47/32* (2013.01)

(58) Field of Classification Search
CPC ........ A61K 38/47; A61K 9/06; A61K 38/164; A61K 47/32; A61K 47/36; Y02A 50/03
See application file for complete search history.

(56) References Cited

U.S. PATENT DOCUMENTS

| | | |
|---|---|---|
| 8,956,602 B2 | 2/2015 | Taft et al. |
| 2018/0117249 A1 | 5/2018 | Pennington et al. |
| 2020/0054574 A1 | 2/2020 | Wang et al. |

OTHER PUBLICATIONS

Dong, Zhenqiang, et al. "H2O2-responsive nanoparticle based on the supramolecular self-assemble of cyclodextrin." Frontiers in Pharmacology 9 (2018): 552. (Year: 2018).*

Saravanakumar G, Kim J, Kim WJ. Reactive-Oxygen-Species-Responsive Drug Delivery Systems: Promises and Challenges. Adv Sci (Weinh). Jun. 8, 2016;4(1):1600124 (Year: 2016).*

(Continued)

*Primary Examiner* — Tracy Vivlemore
*Assistant Examiner* — Thomas R. Amick
(74) *Attorney, Agent, or Firm* — Norton Rose Fulbright US LLP

(57) ABSTRACT

Compositions and methods are provided concerning a lactate-responsive drug release system. In some embodiments, there are methods and compositions for treating cancer that take advantage of the tumor environment to deliver therapeutic agents to the tumor while reducing problems associated with circulating drugs in the patients body.

10 Claims, 14 Drawing Sheets

(56) References Cited

OTHER PUBLICATIONS

Song, Cheng-Cheng, et al. "Oxidation-accelerated hydrolysis of the ortho ester-containing acid-labile polymers." ACS Macro Letters 2.3 (2013): 273-277 (Year: 2013).*
Zhang, Dinglin, et al. "Biocompatible reactive oxygen species (ROS)-responsive nanoparticles as superior drug delivery vehicles." Advanced Healthcare Materials 4.1 (2015): 69-76 (Year: 2015).*
Cui et al., "Facile Synthesis of H202-Cleavable Poly(ester-amide)s by Passerini Multicomponent Polymerization." *ACS Macro Letters* 2016, 6, 11-15.
Ffrench-Constant, R. & Waterfield, N. "An ABC guide to the bacterial toxin complexes." *Advances in applied microbiology* 2006, 58, 169-183.
Hirschhaeuser et al., "Lactate: A Metabolic Key Player in Cancer" *Cancer research* 2011, 71, 6921-6925.
International Search Report and Written Opinion issued in Corresponding PCT Application No. PCT/US2020/070052, dated Sep. 9, 2020.
Kanamala et al., "Mechanisms and biomaterials in pH-responsive tumour targeted drug delivery: a review." *Biomaterials* 2016, 85, 152-167.
Kocak et al., "pH-Responsive polymers." *Polymer Chemistry* 2017, 8, 144-176.
Lin, S. & Theato, P. "CO2-Responsive Polymers." *Macromolecular Rapid Communications* 2013, 34, 1118-1133.
Lu et al. "Stimuli-responsive nanomaterials for therapeutic protein delivery." *J Control Release* 2014, 194, 1-19.
Marchiq, I. & Pouysségur, J. "Hypoxia, cancer metabolism and the therapeutic benefit of targeting lactate/H+ symporters." *Journal of Molecular Medicine* 2016, 94, 155-171.
Mura et al., "Stimuli-responsive nanocarriers for drug delivery." *Nature Materials* 2013, 12, 991-1003.
Romero-Garcia et al. "Lactate Contribution to the Tumor Microenvironment: Mechanisms, Effects on Immune Cells and Therapeutic Relevance" Frontiers in Immunology 2016, 7, 1-11.
San-Millán, I. & Brooks, G. A. "Reexamining cancer metabolism: lactate production for carcinogenesis could be the purpose and explanation of the Warburg Effect." *Carcinogenesis* 2017, 38, 119-133.
Tseng et al. "Targeting Tumor Microenvironment by Bioreduction-Activated Nanoparticles for Light-Triggered Virotherapy" ACS Nano. 2018, 12, 9894-9902.
Yan et al., "Manipulation of block copolymer vesicles using CO 2: dissociation or "breathing"" *Soft Matter* 2013, 9, 2011-2016.
Yu et al., "H2O2-responsive theranostic nanomedicine." *Chinese Chemical Letters* 2017, 28, 1841-1850.
Amoozgar et al. "Low molecular-weight chitosan as a pH-sensitive stealth coating for tumor-specific drug delivery", *Mol Pharm.* 9(5), pp. 1262-1270, 2012.
Office Action issued in corresponding Chinese Application No. 202080051046.6, dated Jul. 22, 2023.

* cited by examiner

Lactate Oxidase $$\text{L-Lactate} + O_2 \xrightarrow{\text{Lactate Oxidase}} \text{Pyruvate} + H_2O_2$$

lactate dehydrogenase $$\text{lactate} + NAD^+ \rightleftharpoons \text{pyruvate} + NADH + H^+$$

lactate 2-monooxygenase $$\text{(S)-lactate} + O_2 \rightleftharpoons \text{acetate} + CO_2 + H_2O$$

*FIG. 1*

The material of the matrix can respond to enzymatic products of lactate.

The lactate-reacting enzymes can be entrapped and/or covalently linked to the matrix.

Lactate responsive system $$\text{L-Lactate} + O_2 \xrightarrow{\text{Lactate Oxidase}} \text{Pyruvate} + H_2O_2$$

$$H_2O_2 \rightleftharpoons H^+ + O_2H^-$$

FIG. 4A-B

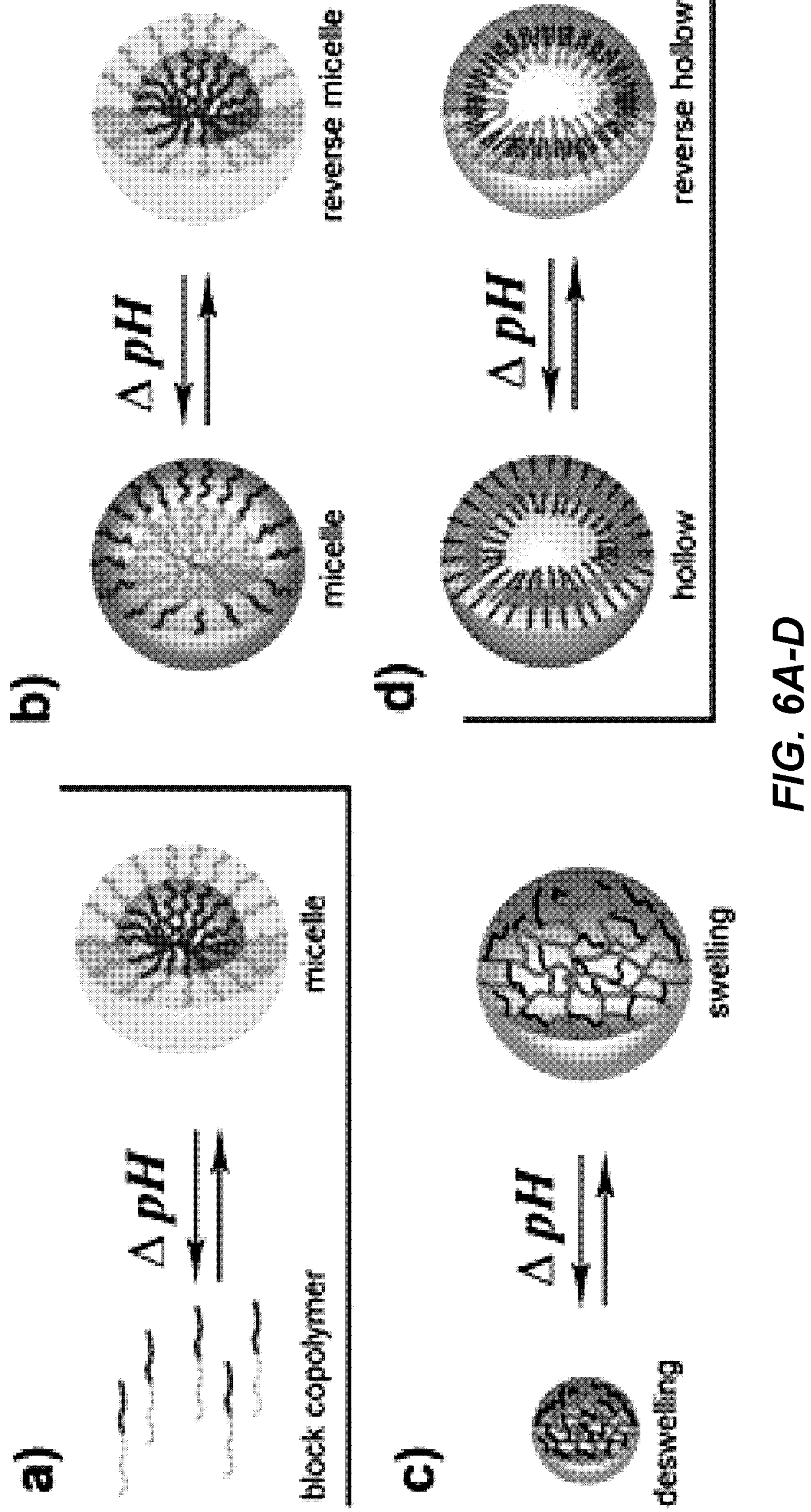
FIG. 6A-D

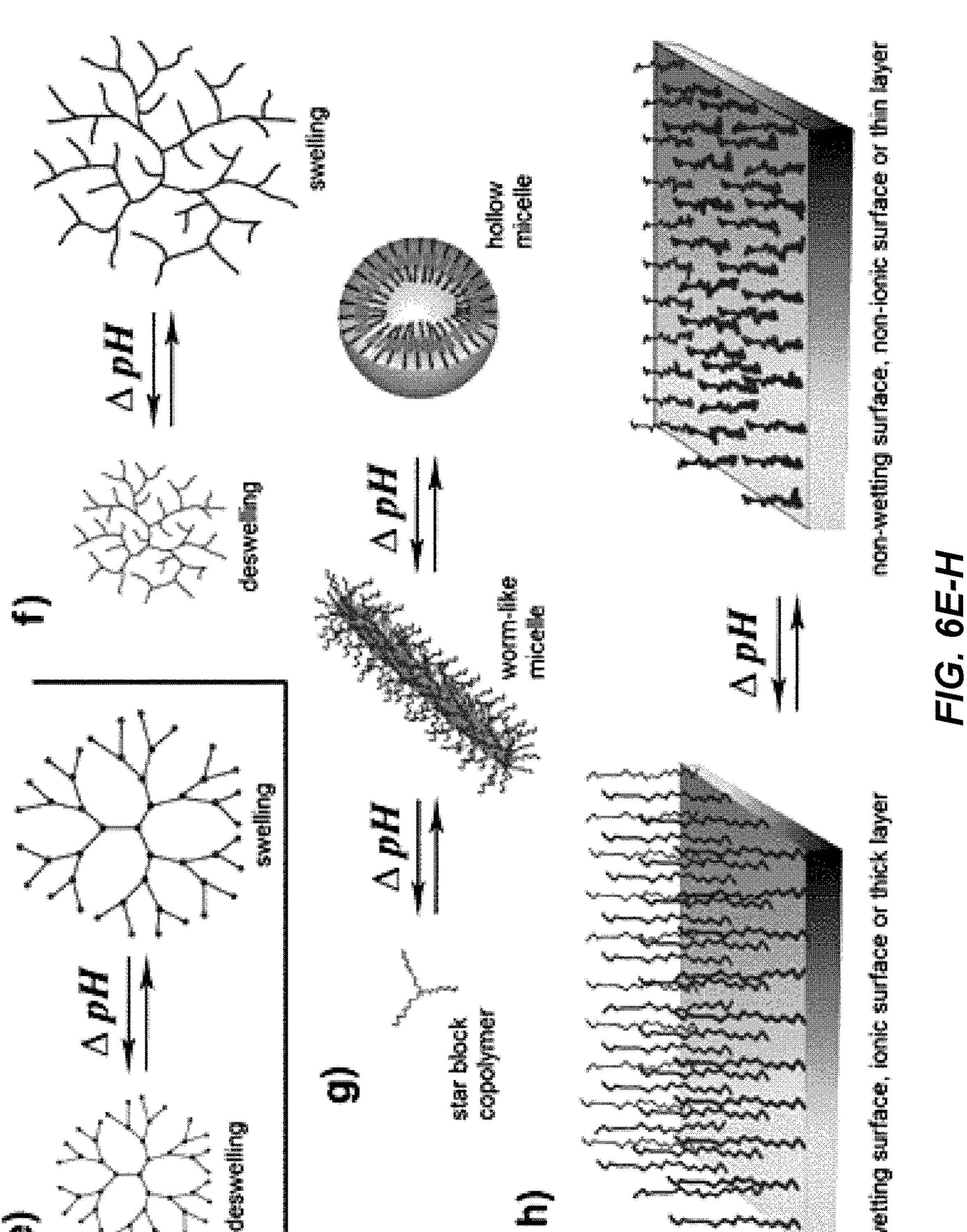
FIG. 6E-H

LACTATE RESPONSE SYSTEM AND METHODS

CROSS-REFERENCE TO RELATED APPLICATIONS

This application is a national phase application under 35 U.S.C. § 371 of International Application No. PCT/US2020/070052 filed May 15, 2020, which claims the benefit of priority of U.S. Provisional Patent Application No. 62/848,432 filed May 15, 2019, which are hereby incorporated by reference in their entirety.

STATEMENT OF GOVERNMENTAL SUPPORT

This invention was made with government support under grant number R01 OD023700 awarded by the National Institutes of Health. The government has certain rights in the invention.

BACKGROUND OF THE INVENTION

1. Field of the Invention

The present invention concerns oncology, bioformulations, and drug delivery. More specifically, it concerns embodiments involving enzymes that are reactant to lactate or other agents that are in higher concentrations in the tumor environment than in a normal, non-tumor environment.

2. Description of Related Art

Lactate plays many roles in the body. It can serve many useful functions, such as fueling the heart, brain, and skeletal muscles. Cancer cells also create and release lactate in large amounts. In oncology, the well-known "Warburg effect" refers to the phenomenon that cancer cells preferentially use aerobic glycolysis rather than oxidative phosphorylation pathway to generate energy. In glycolytic tumors, lactate levels of cancer cells are remarkably elevated up to a 40-fold and are highly correlated with cancer aggressiveness and poor survival.[1] Accumulation of lactate is a common feature of cancer cells.[2]

Traditional chemotherapy faces many challenges for cancer treatment, such as poor selectivity to target tumor cells. Specific stimuli-triggered drug delivery system is a promising approach to resolve this issue and improve therapeutic outcomes.[3,4] For instance, pH triggered delivery system can improve the selectivity by recognizing the acidic extracellular microenvironment of solid tumors.[5] However, many studies have shown that lactate accumulation in cancer site is not necessarily associated with tissue acidosis, thus limiting its applicability in vivo.[6]

In this disclosure, there are embodiments for a tumor-specific drug delivery system that can respond to the lactate accumulation in tumor microenvironment and address problems associated with poor delivery of cancer therapeutics by better targeting cancer cells or a tumor.

SUMMARY OF THE DISCLOSURE

A variety of methods and compositions for enabling lactate-triggered drug delivery are disclosed herein. The methods may be used in a range of applications such as cancer treatment, diagnosis, tracking and biosensors. Particularly, lactate reacting enzymes are introduced into polymeric-based or other chemical-based matrix that can reversibly or irreversibly alter their physicochemical characteristics in response to environmental lactate concentration changes. Different enzymes can carry out different catalytic reactions of lactate, which can be used to stimulate changes in the matrix. The lactate-reacting enzymes include but are not limited to those described in FIG. 1.

Compositions and methods are provided herein. In some embodiments, there is a lactate-triggered, benefit agent release composition comprising a chemical-responsive matrix, at least one lactate reacting enzyme provided within the chemical-responsive matrix, and at least one benefit agent provided within the chemical-responsive matrix. In some aspects, the lactate reacting enzyme is capable of converting a lactate substrate into at least one signaling molecule, and the at least one signaling molecule is capable of altering at least one physicochemical characteristic of the chemical responsive matrix that induces release of the at least one benefit agent. A "benefit agent" is defined as a compound or ingredient that imparts an overall health or therapeutic benefit to a patient. The benefit agent may be a therapeutic agent or a diagnostic agent. In some aspects, the therapeutic agent is a small molecule, a peptide or polypeptide, a nucleic acid, microparticle, nanoparticle, ion, salt, bacteria, virus, live cells, a radiopharmaceutical, chemotherapeutic, an immunotherapeutic, a gene therapy agent, toxin, or a radiotherapeutic. The immunotherapeutic may be an antibody-based agent or an immune checkpoint inhibitor, in some aspects. In some embodiments, the at least one physicochemical characteristic is a reversible physiochemical characteristic. The at least one physicochemical characteristic may be one or more characteristics selected from the group consisting of protonation, deprotonation, bond cleavage, swelling, deswelling, dissociation, and coalescence. In some embodiments, at least a portion of a lactate reacting enzyme population covalently attached to the chemical-responsive matrix. In some embodiments, at least a portion of a lactate reacting enzyme population is conjugated to the chemical-responsive matrix via hydrogen bonds. In some embodiments, at least a portion of a lactate reacting enzyme population is conjugated to the chemical-responsive matrix via ionic bonds.

In some aspects, the at least one signaling molecule is selected from the group consisting of $O_2$, $CO_2$, $H_2O_2$, and $H^+$. In embodiments, the lactate reacting enzyme is selected from the group consisting of lactate oxidase, lactate dehydrogenase, lactate racemase, and lactate 2-monooxygenase. In some aspects, the composition comprises at least a portion of a lactate reacting enzyme population on a composition surface. In some aspects, the composition includes no lactate reacting enzyme on a composition surface. In embodiments, the composition comprises at least a portion of a lactate reacting enzyme population embedded within the chemical-responsive matrix. In some aspects, the composition includes no lactate reacting enzyme embedded within the chemical-responsive matrix.

In embodiments, the chemical-responsive matrix includes at least one functional group capable of reacting with the at least one signaling molecule. In some aspects, the chemical-responsive matrix comprises a material selected from the consisting of chitosan, cyclodextrin, poly-cyclodextrin, poly[(2-dimethylamino) ethyl methacrylate], poly[(2-diethylamino) ethyl methacrylate], poly[(2-diisopropylamino) ethyl methacrylate], poly(4-vinylpyridine), and poly(2-vinylpyridine). In some embodiments, the composition comprises an architecture selected from the group consisting of nanoparticle, microparticle, hydrogel, micelle, unimer micelle, reverse micelle, nanogel, microgel, worm-like micelle, hollow micelle, reverse hollow micelle, dendrimer, graft polymer, star polymer, branched polymer, and brush polymer.

The lactate-triggered, benefit agent release composition may be in the form of an AB toxin complex that comprises an A component and a B component or a modified B component. In some aspects, the modified B component is at least 50, 60, 70, 80, 90%, or more homologous to a B component and comprises a region that interacts with an A component from the AB toxin complex. In some aspects, the B component is from Cholera toxin, Diptheria toxin, Pertussis toxin, *E. coli* heat-labile toxin LT, Shiga toxin, *Pseudomonas* exotoxin A, Botulinum, toxin, Tetanus toxin, Anthrax toxin LF, *Bortella pertussis* AC, *Bacillus anthracis* EF, or *Staphylococcus aureus* Exfoliatin B. In some aspects, the B component is PA, LF, or modified LF from Anthrax toxin.

In some aspects, the amount of the B component in the composition is about 0.001 to about 500 μg per mg of chemical matrix. The composition may include, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 60, 70, 80, 90, 100, 200, 300, 400, to about 500 μg of component B, or any value in between the foregoing. In some embodiments, the chemical-responsive matrix and the at least one lactate reacting enzyme are provided in a mass ratio ranging from 1:1 to 100,000:1. The chemical-responsive matrix and the at least one lactate reacting enzyme may be provided in a mass ratio of 1:1, 10:1, 20:1, 30:1, 40:1, 50:1, 60:1, 70:1, 80:1, 80:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 10,000:1, 20,000:1, 30,000:1, 40,000:1, 50,000:1, 60,000:1, 70,000:1, 80,000:1, 90,000:1, 100,000:1, or any range derivable therein. In embodiments, the chemical-responsive matrix and the at least one benefit agent are provided in a mass ratio ranging from 1:1 to 100,000:1. The chemical-responsive matrix and the at least one benefit agent may be provided in a mass ratio of 1:1, 10:1, 20:1, 30:1, 40:1, 50:1, 60:1, 70:1, 80:1, 80:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 10,000:1, 20,000:1, 30,000:1, 40,000:1, 50,000:1, 60,000:1, 70,000:1, 80,000:1, 90,000:1, 100,000:1, or any range derivable therein. In some aspects, the composition comprises 0.001 μmol to 10,000 μmol of lactate reacting enzyme per gram of chemical-responsive matrix. The composition may comprise 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000 μmol of lactate reacting enzyme per gram of chemical-responsive matrix, or any value in between the foregoing. In some aspects, the benefit agent release composition releases at least $0.1\times10^{10}$ g of benefit agent per gram of chemical-responsive matrix. In some embodiments, the composition comprises 0.001 μg to 500 μg of benefit agent per mg of chemical-responsive matrix. The composition may comprise 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 60, 70, 80, 90, 100, 200, 300, 400, or 500 μg of benefit agent per mg of chemical-responsive matrix, or any value in between the foregoing. In embodiments, the composition comprises 0.001 μg to 500 μg of chemotherapeutic agent per mg of chemical-responsive matrix. The composition may comprise 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 60, 70, 80, 90, 100, 200, 300, 400, or 500 μg of chemotherapeutic agent per mg of chemical-responsive matrix, or any value in between the foregoing. In some aspects, the chemical-responsive matrix and the at least one chemotherapeutic agent are provided in a mass ratio ranging from 1:1 to 100,000:1. The chemical-responsive matrix and the least one chemotherapeutic agent may be provided in a mass ratio of 1:1, 10:1, 20:1, 30:1, 40:1, 50:1, 60:1, 70:1, 80:1, 80:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 10,000:1, 20,000:1, 30,000:1, 40,000:1, 50,000:1, 60,000:1, 70,000:1, 80,000:1, 90,000:1, 100,000:1, or any range derivable therein.

In some embodiments, there are methods for delivering a benefit agent to a lactate target area of a subject to be treated, the method comprising: providing a benefit agent release composition comprising a chemical-responsive matrix, at least one lactate reacting enzyme provided within the chemical-responsive matrix, and at least one benefit agent provided within the chemical-responsive matrix, wherein the lactate reacting enzyme converts a lactate substrate into at least one signaling molecule when the benefit agent release composition is exposed to a lactate concentration that is higher than ambient physiological lactate concentration, and wherein the signaling molecule alters at least one physicochemical characteristic of the chemical responsive matrix and induces release of the at least one benefit agent, wherein the lactate target area has a lactate concentration that is higher than ambient physiological lactate concentration.

In some embodiments, there are methods for treating cancer with a chemotherapeutic agent, the method comprising: providing a chemotherapeutic agent release composition comprising a chemical-responsive matrix, at least one lactate reacting enzyme provided within the chemical-responsive matrix, and at least one chemotherapeutic agent provided within the chemical-responsive matrix, wherein the lactate reacting enzyme converts a lactate substrate into at least one signaling molecule when the chemotherapeutic agent release composition is exposed to a lactate concentration that is higher than ambient physiological lactate concentration, and wherein the signaling molecule alters at least one physicochemical characteristic of the chemical responsive matrix and induces release of the at least one chemotherapeutic agent, wherein the lactate target area has a lactate concentration that is higher than ambient physiological lactate concentration.

In some embodiments, release of the at least one benefit agent targets a benefit agent release to an area comprising higher than ambient physiological lactate concentration. In some aspects, the area comprising higher than ambient physiological lactate concentration is a tumor microenvironment. In some aspects, a chemical-responsive matrix functional group reacts with the at least one signaling molecule. In some embodiments, the at least one physicochemical characteristic is at least one of protonation, deprotonation, bond cleavage, swelling, deswelling, dissociation, and coalescence. In some aspects, the at least one physicochemical characteristic is a reversible physicochemical characteristic. In embodiments, the chemotherapeutic agent release composition comprises an architecture selected from the group consisting of nanoparticle, microparticle, hydrogel, micelle, unimer micelle, reverse micelle, nanogel, microgel, worm-like micelle, hollow micelle, reverse hollow micelle, dendrimer, graft polymer or copolymer, star polymer or copolymer, branched polymer or copolymer, and brush polymer or copolymer. In some aspects, the chemical-responsive matrix comprises a material selected from the consisting of chitosan, cyclodextrin, poly-cyclodextrin, poly [(2-dimethylamino) ethyl methacrylate], poly[(2-diethylamino) ethyl methacrylate], poly[(2-diisopropylamino) ethyl methacrylate], poly(4-vinylpyridine) and poly(2-vinylpyridine).

In some embodiments, the lactate reacting enzyme is selected from the group consisting of lactate oxidase, lactate dehydrogenase, lactate racemase, and lactate 2-monooxygenase. In some embodiments, the chemotherapeutic agent release composition comprises at least a portion of a lactate reacting enzyme population on a composition surface. In some aspects, the chemotherapeutic agent release composition comprises at least a portion of a lactate reacting enzyme population embedded within the chemical-responsive matrix. In some aspects, the chemotherapeutic agent release composition comprises at least a portion of a lactate reacting enzyme population copnjugated to the chemical-responsive matrix through hydrogen bonds. In some aspects, the chemotherapeutic agent release composition comprises at least a portion of a lactate reacting enzyme population conjugated to the chemical-responsive matrix through ionic bonds. In some aspects, the chemotherapeutic agent release composition comprises at least a portion of a lactate reacting enzyme population covalently attached to the chemical-responsive matrix. In some embodiments, the benefit agent release composition releases the at least one benefit agent in a lactate-dose dependent manner. In some aspects, the benefit agent release composition releases at least about $0.1\times10^{-4}$ g of chemotherapeutic agent per gram of chemical-responsive matrix. The benefit agent release composition may release at least about $0.1\times10^{-4}$, $0.2\times10^{-4}$, $0.3\times10^{-4}$, $0.4\times10^{-4}$, $0.5\times10^{-4}$, $0.6\times10^{-4}$, $0.7\times10^{-4}$, $0.8\times10^{-4}$, $0.9\times10^{-4}$, $1\times10^{-4}$, $2\times10^{-4}$, $3\times10^{-4}$, $4\times10^{-4}$, $5\times10^{-4}$, $6\times10^{-4}$, $7\times10^{-4}$, $8\times10^{-4}$, $9\times10^{-4}$, $1\times10^{-3}$, $2\times10^{-3}$, $3\times10^{-3}$, $4\times10^{-3}$, $5\times10^{-3}$, $6\times10^{-3}$, $7\times10^{-3}$, $8\times10^{-3}$, $9\times10^{-3}$, or $1\times10^{-2}$ g of chemotherapeutic agent per gram of chemical-responsive matrix. In embodiments, the chemotherapeutic agent release composition releases at least 30% more chemotherapeutic agent in the presence of lactate than in the absence of lactate. The chemotherapeutic agent release composition may release at least about 30%, 40%, 50%, 60%, 70%, 80%, 90%, 100%, 200%, 300%, 400%, 500%, 600%, 700%, 800%, 900%, 1,000%, 2,000%, 3,000%, 4,000%, 5,000%, 6,000%, 7,000%, 8,000%, 9,000%, or 10,000% more chemotherapeutic agent in the presence of lactate than in the absence of lactate. In some embodiments, the chemical-responsive matrix and the at least one lactate reacting enzyme are provided in a mass ratio ranging 1:1 to 100,000:1. The chemical-responsive matrix and the at least one lactate reacting enzyme may be provided in a mass ratio of 1:1, 10:1, 20:1, 30:1, 40:1, 50:1, 60:1, 70:1, 80:1, 80:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 10,000:1, 20,000:1, 30,000:1, 40,000:1, 50,000:1, 60,000:1, 70,000:1, 80,000:1, 90,000:1, 100,000:1, or any range derivable therein. In some aspects, the chemical-responsive matrix and at least one chemotherapeutic agent are provided in a mass ratio ranging from 1:1 to 100,000:1. In some embodiments, the composition comprises 0.001 μmol to 10,000 μmol of lactate reacting enzyme per gram of chemical-responsive matrix. The chemical-responsive matrix and the least one chemotherapeutic agent may be provided in a mass ratio of 1:1, 10:1, 20:1, 30:1, 40:1, 50:1, 60:1, 70:1, 80:1, 80:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 10,000:1, 20,000:1, 30,000:1, 40,000:1, 50,000:1, 60,000:1, 70,000:1, 80,000:1, 90,000:1, 100,000:1, or any range derivable therein. In some aspects, 0.001 μg to 500 μg of chemotherapeutic agent may be employed per mg of chemical-responsive matrix. The method may employ about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 60, 70, 80, 90, 100, 200, 300, 400, or 500 μg of chemotherapeutic agent per mg of chemical-responsive matrix, or any value in between the foregoing.

In some aspects, the method comprises administering a toxin component A of an AB Toxin Complex, and wherein the at least one chemotherapeutic agent comprises a B component or a modified B component from an AB Toxin Complex, wherein the modified B component is at least 50, 60, 70, 80, 90%, or more homologous to a B component and comprises a region that interacts with an A component from the AB Toxin Complex. In some embodiments, toxin component A is infused into the blood of the patient. Toxin component A may be administered to the patient at least or at most 1, 3, 6, 12, 24, 36, 48, 60, 72, 84, 96, 108, 120, 132, 148, 160 hours or more after the composition is administered to the patient. In embodiments, toxin component A is administered to the patient at least or at most 1, 3, 6, 12, 24, 36, 48, 60, 72, 84, 96, 108, 120, 132, 148, 160 hours or more after the composition is administered to the patient. In some aspects, toxin component A and toxin component B bind in or around a tumor of the patient.

In some embodiments, there are methods of making such compositions by incorporating or combining one or more lactate reacting enzymes into or with a chemical-responsive matrix. In some embodiments, one or more lactate reacting enzymes are linked to a chemical-responsive matrix by chemical and/or physical bonds. Example of physical bonds include ionic bonds and hydrogen bonds.

The term "treatment" or "treating" means any treatment of a disease or disorder in a mammal, including: preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms. In particular embodiments the disease is cancer, which may or may not be characterized by one or more tumors.

As used herein, "pharmaceutically acceptable carrier" or "pharmaceutically acceptable excipient" includes any and all solvents, dispersion media, coatings, antibacterial and antifungal agents, isotonic and absorption delaying agents and the like. In several embodiments, these media and agents can be used in combination with pharmaceutically active substances. Except insofar as any conventional media or agent is incompatible with the active ingredient, its use in the therapeutic compositions is contemplated. Supplementary active ingredients can also be incorporated into the compositions. Any composition or agent discussed herein may implemented with or in a pharmaceutically acceptable carrier or pharmaceutically acceptable excipient.

The terms "effective amount" or "therapeutically effective amount" refer to that amount of a composition of the disclosure that is sufficient to effect treatment, as defined herein, when administered to a mammal in need of such treatment. This amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art. In particular embodiments, an effective amount refers to an amount in the context of effecting treatment for cancer or a tumor.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." Is is specifically contemplated that x, y, or z may be specifically excluded from an embodiment.

Throughout this application, the term "about" is used according to its plain and ordinary meaning in the area of cell biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of"

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 A variety of lactate related enzymes and their mediated reactions

FIG. 6A-H pH-Responsive polymer matrixes of different architectures: (A) unimer-micelle, (B) micelle-reverse micelle, (C) nanogels or microgels, (D) hollow-reverse hollow, (E) dendrimer, (F) hyper-branched, (G) micelle morphology changes (from worm-like to hollow), and (H) polymer brushes.

DETAILED DESCRIPTION

Figure 2:
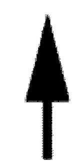
FIG. 2 The composition and design of the lactate responsive system.

The present disclosure provides methods and compositions relating to lactate-responsive drug release systems. The lactate-responsive drug release systems disclosed herein includes a polymeric material or other chemical matrix that may be provided in the form of a particle, hydrogel, or a material that adheres to a substrate, e.g., an electrode substrate. Enzymes may be non-covalently entrapped in the polymeric material or other chemical matrix and/or covalently linked to the polymeric material or other chemical matrix. The drug release system responds to lactate by detecting the product of enzymatic conversion of lactate, including but not limited to, pH changes ($H^+$), $CO_2$ production, $H_2O_2$ production, and $O_2$ production. The methods and compositions may be used for treating cancer by responding to the chemical environment in the vicinity of a tumor. Upon being triggered by a chemical signal in the tumor environment, the compositions can deliver therapeutic agents to the local tumor environment. The methods and compositions address problems associated with systemic administration of drugs and circulation of those drugs within the whole of a patient's body.

As used herein, "reversible" is defined as capable of being reversed so that the previous state or condition is restored. A "nanoparticle" is defined as a particle of any shape with dimensions ranging from about 1 nm to about 100 nm. A "microparticle" is defined as a particle of any shape with dimensions ranging from between about 1 μm to about 1,000 μm. A "gel" is defined as non-fluid colloidal network or polymer network that is expanded throughout its whole volume by a fluid. A "hydrogel" is defined as a gel in which the swelling agent is water. A "micelle" is defined as an aggregate or assembly of surfactant molecules dispersed in a liquid. A "reverse micelle" is defined as a micelle in which polar groups of surfactants are concentrated in the interior and lipophilic groups extend towards and into a non-polar solvent. A "reverse hollow micelle" is a reverse micelle whose interior is hollow. A "dendrimer" is defined as a molecule with repetitively branching structure. A "graft polymer" is defined as a segmented copolymer with a linear backbone of one composite and randomly distributed branches of another composite. A "branched polymer" is defined as a polymer having secondary polymer chains linked to a primary backbone. A "star polymer" is defined as a branched polymer whose general structure includes multiple (at least three) linear chains connected to a central core. A "brush polymer" is a polymer having a main chain (backbone) with multiple branch points (at least three) from which linear side-chains eminate.

I. ANTIBODIES

Aspects of the disclosure relate to the use of anti-inflammatory antibodies or fragments thereof. The term "antibody" refers to an intact immunoglobulin of any isotype, or a fragment thereof that can compete with the intact antibody for specific binding to the target antigen, and includes chimeric, humanized, fully human, and bispecific antibodies. As used herein, the terms "antibody" or "immunoglobulin" are used interchangeably and refer to any of several classes of structurally related proteins that function as part of the immune response of an animal, including IgG, IgD, IgE, IgA, IgM, and related proteins, as well as polypeptides comprising antibody CDR domains that retain antigen-binding activity.

The term "antigen" refers to a molecule or a portion of a molecule capable of being bound by a selective binding agent, such as an antibody. An antigen may possess one or more epitopes that are capable of interacting with different antibodies.

The term "epitope" includes any region or portion of molecule capable eliciting an immune response by binding to an immunoglobulin or to a T-cell receptor. Epitope determinants may include chemically active surface groups such as amino acids, sugar side chains, phosphoryl or sulfonyl groups, and may have specific three-dimensional structural characteristics and/or specific charge characteristics. Generally, antibodies specific for a particular target antigen will preferentially recognize an epitope on the target antigen within a complex mixture.

The epitope regions of a given polypeptide can be identified using many different epitope mapping techniques are well known in the art, including: x-ray crystallography, nuclear magnetic resonance spectroscopy, site-directed mutagenesis mapping, protein display arrays, see, e.g., Epitope Mapping Protocols, (Johan Rockberg and Johan Nilvebrant, Ed., 2018) Humana Press, New York, N.Y. Such techniques are known in the art and described in, e.g., U.S. Pat. No. 4,708,871; Geysen et al. Proc. Natl. Acad. Sci. USA 81:3998-4002 (1984); Geysen et al. Proc. Natl. Acad. Sci. USA 82:178-182 (1985); Geysen et al. Molec. Immunol. 23:709-715 (1986 See, e.g., Epitope Mapping Protocols, supra. Additionally, antigenic regions of proteins can also be predicted and identified using standard antigenicity and hydropathy plots.

An intact antibody is generally composed of two full-length heavy chains and two full-length light chains, but in some instances may include fewer chains, such as antibodies naturally occurring in camelids that may comprise only heavy chains. Antibodies as disclosed herein may be derived solely from a single source or may be "chimeric," that is, different portions of the antibody may be derived from two different antibodies. For example, the variable or CDR regions may be derived from a rat or murine source, while the constant region is derived from a different animal source, such as a human. The antibodies or binding fragments may be produced in hybridomas, by recombinant DNA techniques, or by enzymatic or chemical cleavage of intact antibodies. Unless otherwise indicated, the term "antibody" includes derivatives, variants, fragments, and muteins thereof, examples of which are described below (Sela-Culang et al. Front Immunol. 2013; 4: 302; 2013)

The term "light chain" includes a full-length light chain and fragments thereof having sufficient variable region sequence to confer binding specificity. A full-length light chain has a molecular weight of around 25,000 Daltons and includes a variable region domain (abbreviated herein as VL), and a constant region domain (abbreviated herein as CL). There are two classifications of light chains, identified as kappa (κ) and lambda (λ). The term "VL fragment" means a fragment of the light chain of a monoclonal antibody that includes all or part of the light chain variable region, including CDRs. A VL fragment can further include light chain constant region sequences. The variable region domain of the light chain is at the amino-terminus of the polypeptide.

The term "heavy chain" includes a full-length heavy chain and fragments thereof having sufficient variable region sequence to confer binding specificity. A full-length heavy chain has a molecular weight of around 50,000 Daltons and includes a variable region domain (abbreviated herein as VH), and three constant region domains (abbreviated herein as CH1, CH2, and CH3). The term "VH fragment" means a fragment of the heavy chain of a monoclonal antibody that includes all or part of the heavy chain variable region, including CDRs. A VH fragment can further include heavy chain constant region sequences. The number of heavy chain constant region domains will depend on the isotype. The VH domain is at the amino-terminus of the polypeptide, and the CH domains are at the carboxy-terminus, with the CH3 being closest to the —COOH end. The isotype of an antibody can be IgM, IgD, IgG, IgA, or IgE and is defined by the heavy chains present of which there are five classifications: mu (μ), delta (δ), gamma (γ), alpha (α), or epsilon (ε) chains, respectively. IgG has several subtypes, including, but not limited to, IgG1, IgG2, IgG3, and IgG4. IgM subtypes include IgM1 and IgM2. IgA subtypes include IgA1 and IgA2.

Antibodies can be whole immunoglobulins of any isotype or classification, chimeric antibodies, or hybrid antibodies with specificity to two or more antigens. They may also be fragments (e.g., F(ab')2, Fab', Fab, Fv, and the like), including hybrid fragments. An immunoglobulin also includes natural, synthetic, or genetically engineered proteins that act like an antibody by binding to specific antigens to form a complex. The term antibody includes genetically engineered or otherwise modified forms of immunoglobulins, such as the following:

The term "monomer" means an antibody containing only one Ig unit. Monomers are the basic functional units of antibodies. The term "dimer" means an antibody containing two Ig units attached to one another via constant domains of the antibody heavy chains (the Fc, or fragment crystallizable, region). The complex may be stabilized by a joining (J) chain protein. The term "multimer" means an antibody containing more than two Ig units attached to one another via constant domains of the antibody heavy chains (the Fc region). The complex may be stabilized by a joining (J) chain protein.

The term "bivalent antibody" means an antibody that comprises two antigen-binding sites. The two binding sites may have the same antigen specificities or they may be bi-specific, meaning the two antigen-binding sites have different antigen specificities.

Bispecific antibodies are a class of antibodies that have two paratopes with different binding sites for two or more distinct epitopes. In some embodiments, bispecific antibodies can be biparatopic, wherein a bispecific antibody may specifically recognize a different epitope from the same antigen. In some embodiments, bispecific antibodies can be constructed from a pair of different single domain antibodies termed "nanobodies". Single domain antibodies are sourced and modified from cartilaginous fish and camelids. Nanobodies can be joined together by a linker using techniques typical to a person skilled in the art; such methods for selection and joining of nanobodies are described in PCT Publication No. WO2015044386A1, No. WO2010037838A2, and Bever et al., Anal Chem. 86:7875-7882 (2014), each of which are specifically incorporated herein by reference in their entirety.

Bispecific antibodies can be constructed as: a whole IgG, Fab'2, Fab'PEG, a diabody, or alternatively as scFv. Diabodies and scFvs can be constructed without an Fc region, using only variable domains, potentially reducing the effects of anti-idiotypic reaction. Bispecific antibodies may be produced by a variety of methods including, but not limited to, fusion of hybridomas or linking of Fab' fragments. See, e.g., Songsivilai and Lachmann, Clin. Exp. Immunol. 79:315-321 (1990); Kostelny et al., J. Immunol. 148:1547-1553 (1992), each of which are specifically incorporated by reference in their entirety.

In certain aspects, the antigen-binding domain may be multispecific or heterospecific by multimerizing with VH and VL region pairs that bind a different antigen. For example, the antibody may bind to, or interact with, (a) a cell surface antigen, (b) an Fc receptor on the surface of an effector cell, or (c) at least one other component. Accordingly, aspects may include, but are not limited to, bispecific, trispecific, tetraspecific, and other multispecific antibodies or antigen-binding fragments thereof that are directed to epitopes and to other targets, such as Fc receptors on effector cells.

In some embodiments, multispecific antibodies can be used and directly linked via a short flexible polypeptide chain, using routine methods known in the art. One such example is diabodies that are bivalent, bispecific antibodies in which the VH and VL domains are expressed on a single polypeptide chain, and utilize a linker that is too short to allow for pairing between domains on the same chain, thereby forcing the domains to pair with complementary domains of another chain creating two antigen binding sites. The linker functionality is applicable for embodiments of triabodies, tetrabodies, and higher order antibody multimers. (see, e.g., Hollinger et al., Proc Natl. Acad. Sci. USA 90:6444-6448 (1993); Polijak et al., Structure 2:1121-1123 (1994); Todorovska et al., J. Immunol. Methods 248:47-66 (2001)).

Bispecific diabodies, as opposed to bispecific whole antibodies, may also be advantageous because they can be readily constructed and expressed in *E. coli*. Diabodies (and other polypeptides such as antibody fragments) of appropriate binding specificities can be readily selected using phage display (WO94/13804) from libraries. If one arm of the diabody is kept constant, for instance, with a specificity directed against a protein, then a library can be made where the other arm is varied and an antibody of appropriate specificity selected. Bispecific whole antibodies may be made by alternative engineering methods as described in Ridgeway et al., (Protein Eng., 9:616-621, 1996) and Krah et al., (N Biotechnol. 39:167-173, 2017), each of which is hereby incorporated by reference in their entirety.

Heteroconjugate antibodies are composed of two covalently linked monoclonal antibodies with different specificities. See, e.g., U.S. Pat. No. 6,010,902, incorporated herein by reference in its entirety.

The part of the Fv fragment of an antibody molecule that binds with high specificity to the epitope of the antigen is referred to herein as the "paratope." The paratope consists of the amino acid residues that make contact with the epitope of an antigen to facilitate antigen recognition. Each of the two Fv fragments of an antibody is composed of the two variable domains, VH and VL, in dimerized configuration. The primary structure of each of the variable domains includes three hypervariable loops separated by, and flanked by, Framework Regions (FR). The hypervariable loops are the regions of highest primary sequences variability among the antibody molecules from any mammal. The term hypervariable loop is sometimes used interchangeably with the term "Complementarity Determining Region (CDR)." The length of the hypervariable loops (or CDRs) varies between antibody molecules. The framework regions of all antibody molecules from a given mammal have high primary sequence similarity/consensus. The consensus of framework regions can be used by one skilled in the art to identify both the framework regions and the hypervariable loops (or CDRs) which are interspersed among the framework regions. The hypervariable loops are given identifying names which distinguish their position within the polypeptide, and on which domain they occur. CDRs in the VL domain are identified as L1, L2, and L3, with L1 occurring at the most distal end and L3 occurring closest to the CL domain. The CDRs may also be given the names CDR-1, CDR-2, and CDR-3. The L3 (CDR-3) is generally the region of highest variability among all antibody molecules produced by a given organism. The CDRs are regions of the polypeptide chain arranged linearly in the primary structure, and separated from each other by Framework Regions. The amino terminal (N-terminal) end of the VL chain is named FR1. The region identified as FR2 occurs between L1 and L2 hypervariable loops. FR3 occurs between L2 and L3 hypervariable loops, and the FR4 region is closest to the CL domain. This structure and nomenclature is repeated for the VH chain, which includes three CDRs identified as H1, H2 and H3. The majority of amino acid residues in the variable domains, or Fv fragments (VH and VL), are part of the framework regions (approximately 85%). The three dimensional, or tertiary, structure of an antibody molecule is such that the framework regions are more internal to the molecule and provide the majority of the structure, with the CDRs on the external surface of the molecule.

Several methods have been developed and can be used by one skilled in the art to identify the exact amino acids that constitute each of these regions. This can be done using any of a number of multiple sequence alignment methods and algorithms, which identify the conserved amino acid residues that make up the framework regions, therefore identifying the CDRs that may vary in length but are located between framework regions. Three commonly used methods have been developed for identification of the CDRs of antibodies: Kabat (as described in T. T. Wu and E. A. Kabat, "AN ANALYSIS OF THE SEQUENCES OF THE VARIABLE REGIONS OF BENCE JONES PROTEINS AND MYELOMA LIGHT CHAINS AND THEIR IMPLICATIONS FOR ANTIBODY COMPLEMENTARITY," J Exp Med, vol. 132, no. 2, pp. 211-250, August 1970); Chothia (as described in C. Chothia et al., "Conformations of immunoglobulin hypervariable regions," Nature, vol. 342, no. 6252, pp. 877-883, December 1989); and IMGT (as described in M.-P. Lefranc et al., "IMGT unique numbering for immunoglobulin and T cell receptor variable domains and Ig superfamily V-like domains," Developmental & Comparative Immunology, vol. 27, no. 1, pp. 55-77, January 2003). These methods each include unique numbering systems for the identification of the amino acid residues that constitute the variable regions. In most antibody molecules, the amino acid residues that actually contact the epitope of the antigen occur in the CDRs, although in some cases, residues within the framework regions contribute to antigen binding.

One skilled in the art can use any of several methods to determine the paratope of an antibody. These methods include: 1) Computational predictions of the tertiary structure of the antibody/epitope binding interactions based on the chemical nature of the amino acid sequence of the antibody variable region and composition of the epitope; 2) Hydrogen-deuterium exchange and mass spectroscopy; 3) Polypeptide fragmentation and peptide mapping approaches in which one generates multiple overlapping peptide fragments from the full length of the polypeptide and evaluates the binding affinity of these peptides for the epitope; 4) Antibody Phage Display Library analysis in which the antibody Fab fragment encoding genes of the mammal are expressed by bacteriophage in such a way as to be incorporated into the coat of the phage. This population of Fab expressing phage are then allowed to interact with the antigen which has been immobilized or may be expressed in by a different exogenous expression system. Non-binding Fab fragments are washed away, thereby leaving only the specific binding Fab fragments attached to the antigen. The binding Fab fragments can be readily isolated and the genes which encode them determined. This approach can also be used for smaller regions of the Fab fragment including Fv fragments or specific VH and VL domains as appropriate.

In certain aspects, affinity matured antibodies are enhanced with one or more modifications in one or more CDRs thereof that result in an improvement in the affinity of the antibody for a target antigen as compared to a parent antibody that does not possess those alteration(s). Certain affinity matured antibodies will have nanomolar or picomolar affinities for the target antigen. Affinity matured antibodies are produced by procedures known in the art, e.g., Marks et al., Bio/Technology 10:779 (1992) describes affinity maturation by VH and VL domain shuffling, random mutagenesis of CDR and/or framework residues employed in phage display is described by Rajpal et al., PNAS. 24: 8466-8471 (2005) and Thie et al., Methods Mol Biol. 525:309-22 (2009) in conjugation with computation methods as demonstrated in Tiller et al., Front. Immunol. 8:986 (2017).

Chimeric immunoglobulins are the products of fused genes derived from different species; "humanized" chimeras generally have the framework region (FR) from human immunoglobulins and one or more CDRs are from a non-human source.

In certain aspects, portions of the heavy and/or light chain are identical or homologous to corresponding sequences from another particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity. U.S. Pat. No. 4,816,567; and Morrison et al., Proc. Natl. Acad. Sci. USA 81:6851 (1984). For methods relating to chimeric antibodies, see, e.g., U.S. Pat. No. 4,816,567; and Morrison et al., Proc. Natl. Acad. Sci. USA 81:6851-6855 (1985), each of which are specifically incorporated herein by reference in their entirety. CDR grafting is described, for example, in U.S. Pat. Nos. 6,180,370, 5,693,762, 5,693,761, 5,585,089, and 5,530,101, which are all hereby incorporated by reference for all purposes.

In some embodiments, minimizing the antibody polypeptide sequence from the non-human species optimizes chimeric antibody function and reduces immunogenicity. Specific amino acid residues from non-antigen recognizing regions of the non-human antibody are modified to be homologous to corresponding residues in a human antibody or isotype. One example is the "CDR-grafted" antibody, in which an antibody comprises one or more CDRs from a particular species or belonging to a specific antibody class or subclass, while the remainder of the antibody chain(s) is identical or homologous to a corresponding sequence in antibodies derived from another species or belonging to another antibody class or subclass. For use in humans, the V region composed of CDR1, CDR2, and partial CDR3 for both the light and heavy chain variance region from a non-human immunoglobulin, are grafted with a human antibody framework region, replacing the naturally occurring antigen receptors of the human antibody with the non-human CDRs. In some instances, corresponding non-human residues replace framework region residues of the human immunoglobulin. Furthermore, humanized antibodies may comprise residues that are not found in the recipient antibody or in the donor antibody to further refine performance. The humanized antibody may also comprise at least a portion of an immunoglobulin constant region (Fc), typically that of a human immunoglobulin. See, e.g., Jones et al., Nature 321:522 (1986); Riechmann et al., Nature 332:323 (1988); Presta, Curr. Op. Struct. Biol. 2:593 (1992); Vaswani and Hamilton, Ann. Allergy, Asthma and Immunol. 1:105 (1998); Harris, Biochem. Soc. Transactions 23; 1035 (1995); Hurle and Gross, Curr. Op. Biotech. 5:428 (1994); Verhoeyen et al., Science 239:1534-36 (1988).

Intrabodies are intracellularly localized immunoglobulins that bind to intracellular antigens as opposed to secreted antibodies, which bind antigens in the extracellular space.

Polyclonal antibody preparations typically include different antibodies against different determinants (epitopes). In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies or "mAb" refer to an antibody obtained from a population of homogeneous antibodies from an exclusive parental cell, e.g., the population is identical except for naturally occurring mutations that may be present in minor amounts. Each monoclonal antibody is directed against a single antigenic determinant.

2. Functional Antibody Fragments and Antigen-Binding Fragments a. Antigen-Binding Fragments Certain aspects relate to antibody fragments, such as antibody fragments that bind to and/or neutralize inflammatory mediators. The term functional antibody fragment includes antigen-binding fragments of an antibody that retain the ability to specifically bind to an antigen. These fragments are constituted of various arrangements of the variable region heavy chain (VH) and/or light chain (VL); and in some embodiments, include constant region heavy chain 1 (CH1) and light chain (CL). In some embodiments, they lack the Fc region constituted of heavy chain 2 (CH2) and 3 (CH3) domains. Embodiments of antigen binding fragments and the modifications thereof may include: (i) the Fab fragment type constituted with the VL, VH, CL, and CH1 domains; (ii) the Fd fragment type constituted with the VH and CH1 domains; (iii) the Fv fragment type constituted with the VH and VL domains; (iv) the single domain fragment type, dAb, (Ward, 1989; McCafferty et al., 1990; Holt et al., 2003) constituted with a single VH or VL domain; (v) isolated complementarity determining region (CDR) regions. Such terms are described, for example, in Harlow and Lane, Antibodies: A Laboratory Manual, Cold Spring Harbor Laboratory, N Y (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, 2d ed., Wiley-Liss, Inc. New York, N.Y. (1990); Antibodies, 4:259-277 (2015). The citations in this paragraph are all incorporated by reference.

Antigen-binding fragments also include fragments of an antibody that retain exactly, at least, or at most 1, 2, or 3 complementarity determining regions (CDRs) from a light chain variable region. Fusions of CDR-containing sequences to an Fc region (or a CH2 or CH3 region thereof) are included within the scope of this definition including, for example, scFv fused, directly or indirectly, to an Fc region are included herein.

The term Fab fragment means a monovalent antigen-binding fragment of an antibody containing the VL, VH, CL and CH1 domains. The term Fab' fragment means a monovalent antigen-binding fragment of a monoclonal antibody that is larger than a Fab fragment. For example, a Fab' fragment includes the VL, VH, CL and CH1 domains and all or part of the hinge region. The term F(ab')2 fragment means a bivalent antigen-binding fragment of a monoclonal antibody comprising two Fab' fragments linked by a disulfide bridge at the hinge region. An F(ab')2 fragment includes, for example, all or part of the two VH and VL domains, and can further include all or part of the two CL and CH1 domains.

The term Fd fragment means a fragment of the heavy chain of a monoclonal antibody, which includes all or part of the VH, including the CDRs. An Fd fragment can further include CH1 region sequences.

The term Fv fragment means a monovalent antigen-binding fragment of a monoclonal antibody, including all or part of the VL and VH, and absent of the CL and CH1 domains. The VL and VH include, for example, the CDRs. Single-chain antibodies (sFv or scFv) are Fv molecules in which the VL and VH regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference. The term (scFv)2 means bivalent or bispecific sFv polypeptide chains that include oligomerization domains at their C-termini, separated from the sFv by a hinge region (Pack et al. 1992). The oligomerization domain comprises self-associating a-helices, e.g., leucine zippers, which can be further stabilized by additional disulfide bonds. (scFv)2 fragments are also known as "miniantibodies" or "minibodies."

A single domain antibody is an antigen-binding fragment containing only a VH or the VL domain. In some instances, two or more VH regions are covalently joined with a peptide linker to create a bivalent domain antibody. The two VH regions of a bivalent domain antibody may target the same or different antigens.

b. Fragment Crystallizable Region, Fc

An Fc region contains two heavy chain fragments comprising the CH2 and CH3 domains of an antibody. The two heavy chain fragments are held together by two or more disulfide bonds and by hydrophobic interactions of the CH3 domains. The term "Fc polypeptide" as used herein includes native and mutein forms of polypeptides derived from the Fc region of an antibody. Truncated forms of such polypeptides containing the hinge region that promotes dimerization are included.

3. Polypeptides with Antibody CDRs & Scaffolding Domains that Display the CDRs

Antigen-binding peptide scaffolds, such as complementarity-determining regions (CDRs), are used to generate protein-binding molecules in accordance with the embodiments. Generally, a person skilled in the art can determine the type of protein scaffold on which to graft at least one of the CDRs. It is known that scaffolds, optimally, must meet a number of criteria such as: good phylogenetic conservation; known three-dimensional structure; small size; few or no post-transcriptional modifications; and/or be easy to produce, express, and purify. Skerra, J Mol Recognit, 13:167-87 (2000).

The protein scaffolds can be sourced from, but not limited to: fibronectin type III FN3 domain (known as "monobodies"), fibronectin type III domain 10, lipocalin, anticalin, Z-domain of protein A of *Staphylococcus aureus*, thioredoxin A or proteins with a repeated motif such as the "ankyrin repeat", the "armadillo repeat", the "leucine-rich repeat" and the "tetratricopeptide repeat". Such proteins are described in US Patent Publication Nos. 2010/0285564, 2006/0058510, 2006/0088908, 2005/0106660, and PCT Publication No. WO2006/056464, each of which are specifically incorporated herein by reference in their entirety. Scaffolds derived from toxins from scorpions, insects, plants, mollusks, etc., and the protein inhibiters of neuronal NO synthase (PIN) may also be used.

II. THERAPEUTIC METHODS

The compositions of the disclosure may be used for in vivo, in vitro, or ex vivo administration. The route of administration of the composition may be, for example, intracutaneous, subcutaneous, intravenous, local, topical, and intraperitoneal administrations. The autoimmune condition or inflammatory condition amenable for treatment may include, but not be limited to conditions such as diabetes (e.g. type 1 diabetes), graft rejection, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis such as spino-optical multiple sclerosis, primary progressive multiple sclerosis (PPMS), and relapsing remitting multiple sclerosis (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, *balanitis* including *balanitis circumscripta* plasmacellularis, balanoposthitis, *erythema annulare centrifugum, erythema* dyschromicum perstans, eythema multiform, granuloma *annulare, lichen nitidus, lichen sclerosus* et *atrophicus, lichen simplex* chronicus, *lichen spinulosus, lichen planus*, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma *bronchiale*, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus *foliaceus*, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, *erythema* multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, *erythema elevatum* et *diutinum*, erythroblastosis *fetalis*, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes *dorsalis*, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, *erythema* nodosum leprosum, idiopathic facial paralysis, chronic fatigue syndrome, *febris* rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

A. Checkpoint Inhibitors and Combination Treatment

Embodiments of the disclosure may include administration of immune checkpoint inhibitors, which are further described below.

1. PD-1, PDL1, and PDL2 inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PDL1 on epithelial cells and tumor cells. PDL2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PDL1 activity.

Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 inhibitor is a molecule that inhibits the binding of PD-1 to its ligand binding partners. In a specific aspect, the PD-1 ligand binding partners are PDL1 and/or PDL2. In another embodiment, a PDL1 inhibitor is a molecule that inhibits the binding of PDL1 to its binding partners. In a specific aspect, PDL1 binding partners are PD-1 and/or B7-1. In another embodiment, the PDL2 inhibitor is a molecule that inhibits the binding of PDL2 to its binding partners. In a specific aspect, a PDL2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some embodiments, the PD-1 inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and pidilizumab. In some embodiments, the PD-1 inhibitor is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PDL1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 inhibitors include MEDI0680, also known as AMP-514, and REGN2810.

In some embodiments, the immune checkpoint inhibitor is a PDL1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the immune checkpoint inhibitor is a PDL2 inhibitor such as rHIgM12B7.

In some embodiments, the inhibitor comprises the heavy and light chain CDRs or VRs of nivolumab, pembrolizumab, or pidilizumab. Accordingly, in one embodiment, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another embodiment, the antibody competes for binding with and/or binds to the same epitope on PD-1, PDL1, or PDL2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

2. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some embodiments, the inhibitor blocks the CTLA-4 and B7-1 interaction. In some embodiments, the inhibitor blocks the CTLA-4 and B7-2 interaction.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156;

Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as a checkpoint inhibitor in the methods and compositions of the disclosure is ipilimumab (also known as 10D1, MDX-010, MDX-101, and Yervoy®) or antigen binding fragments and variants thereof (see, e.g., WO 01/14424).

In some embodiments, the inhibitor comprises the heavy and light chain CDRs or VRs of tremelimumab or ipilimumab. Accordingly, in one embodiment, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another embodiment, the antibody competes for binding with and/or binds to the same epitope on PD-1, B7-1, or B7-2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

III. IMMUNOTHERAPY

In some embodiments, the methods comprise utilization of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumour-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immumotherapies are known in the art, and some are described below.

A. Inhibition of Co-Stimulatory Molecules

In some embodiments, the immunotherapy comprises an inhibitor of a co-stimulatory molecule. In some embodiments, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TNFRSF18), and combinations thereof. Inhibitors include inhibitory antibodies, polypeptides, compounds, and nucleic acids.

B. Dendritic Cell Therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor. Dendritic cell receptors such as TLR3, TLR7, TLR8 or CD40 have been used as antibody targets.

C. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signalling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (Kymriah) and Axicabtagene ciloleucel (Yescarta). In some embodiments, the CAR-T therapy targets CD19.

D. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFNα and IFNβ), type II (IFNγ) and type III (IFNλ).

Interleukins have an array of immune system effects. IL-2 is an exemplary interleukin cytokine therapy.

E. Adoptive T-Cell Therapy

Adoptive T cell therapy is a form of passive immunization by the transfusion of T-cells (adoptive cell transfer). They are found in blood and tissue and usually activate when they find foreign pathogens. Specifically they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumour death.

Multiple ways of producing and obtaining tumour targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

It is contemplated that a cancer treatment may exclude any of the cancer treatments described herein. Furthermore, embodiments of the disclosure include patients that have been previously treated for a therapy described herein, are currently being treated for a therapy described herein, or have not been treated for a therapy described herein. In some embodiments, the patient is one that has been determined to be resistant to a therapy described herein. In some embodiments, the patient is one that has been determined to be sensitive to a therapy described herein.

IV. ADMINISTRATION OF THERAPEUTIC COMPOSITIONS

The therapy provided herein may comprise administration of a combination of therapeutic agents, such as a first cancer therapy and a second cancer therapy. The therapies may be administered in any suitable manner known in the art. For example, the first and second cancer treatment may be administered sequentially (at different times) or concurrently (at the same time). In some embodiments, the first and second cancer treatments are administered in a separate composition. In some embodiments, the first and second cancer treatments are in the same composition.

Embodiments of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some embodiments, the cancer therapy is administered intravenously, intramuscularly, subcutaneously, topically, orally, transdermally, intraperitoneally, intraorbitally, by implantation, by inhalation, intrathecally, intraventricularly, or intranasally. In some embodiments, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 μg/kg, mg/kg, μg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 μM to 150 μM. In another embodiment, the effective dose provides a blood level of about 4 μM to 100 μM; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or mM (blood levels), such as 4 μM to 100

μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

A. Kits

Certain aspects of the present invention also concern kits containing compositions of the invention or compositions to implement methods of the invention. In some embodiments, kits can be used to evaluate one or more biomarkers. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein. In some embodiments, there are kits for evaluating biomarker activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 2×, 5×, 10×, or 20× or more.

Kits for using probes, synthetic nucleic acids, nonsynthetic nucleic acids, and/or inhibitors of the disclosure for prognostic or diagnostic applications are included as part of the disclosure. Specifically contemplated are any such molecules corresponding to any biomarker identified herein, which includes nucleic acid primers/primer sets and probes that are identical to or complementary to all or part of a biomarker, which may include noncoding sequences of the biomarker, as well as coding sequences of the biomarker.

In certain aspects, negative and/or positive control nucleic acids, probes, and inhibitors are included in some kit embodiments. In addition, a kit may include a sample that is a negative or positive control for methylation of one or more biomarkers. In some embodiments, a control includes a nucleic acid that contains at least one CpG or is capable of identifying a CpG methylation site.

It is contemplated that any method or composition described herein can be implemented with respect to any other method or composition described herein and that different embodiments may be combined. The claims originally filed are contemplated to cover claims that are multiply dependent on any filed claim or combination of filed claims.

Any embodiment of the disclosure involving specific biomarker by name is contemplated also to cover embodiments involving biomarkers whose sequences are at least 80, 81, 82, 83, 84, 85, 86, 87, 88, 89, 90, 91, 92, 93, 94, 95, 96, 97, 98, 99% identical to the mature sequence of the specified nucleic acid.

Embodiments of the disclosure include kits for analysis of a pathological sample by assessing biomarker profile for a sample comprising, in suitable container means, two or more biomarker probes, wherein the biomarker probes detect one or more of the biomarkers identified herein. The kit can further comprise reagents for labeling nucleic acids in the sample. The kit may also include labeling reagents, including at least one of amine-modified nucleotide, poly(A) polymerase, and poly(A) polymerase buffer. Labeling reagents can include an amine-reactive dye.

V. CANCER THERAPY

In some embodiments, the method comprises administering a cancer therapy to the patient. The cancer therapy may be chosen based on the expression level measurements, alone or in combination with the clinical risk score calculated for the patient. In some embodiments, the cancer therapy comprises a local cancer therapy. In some embodiments, the cancer therapy excludes a systemic cancer therapy. In some embodiments, the cancer therapy excludes a local therapy. In some embodiments, the cancer therapy comprises a local cancer therapy without the administration of a system cancer therapy. In some embodiments, the cancer therapy comprises an immunotherapy, which may be an immune checkpoint therapy. Any of these cancer therapies may also be excluded. Combinations of these therapies may also be administered. In some embodiments, gene or miRNA expression measurement and analysis may indicate that one or more cancer therapies would be likely to be effective or ineffective. A particular advantage of methods disclosed herein is that they allow doctors for the first time to make a treatment decision based on the molecular subtype of a metastasis.

VI. DIAGNOSING AND TREATING CANCER

Also disclosed is a method of diagnosing and treating a patient having a cancer tumor, the method comprising: (a) obtaining a tissue sample from the metastasis; (b) measuring the expression of one or more genes and/or miRNAs in the sample; (c) comparing the measured expression level of each gene or miRNA to a reference expression level for that gene or miRNA; (d) identifying the metastasis as an SNF1, SNF2, or SNF3-type metastasis based on the measured expression levels; and (e) administering to the patient an appropriate therapy based on the type of metastasis identified in step (d).

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Figure 3:
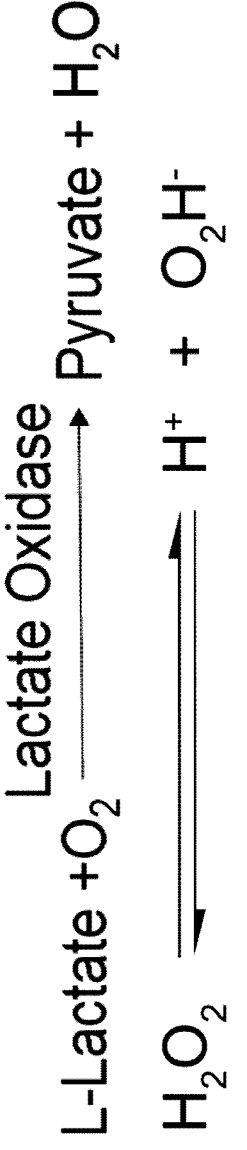
FIG. 3 Enzymatic reactions involving lactate oxidase.

A lactate-responsive drug delivery system represents a novel treatment of a tumor. In the first example, the inventors developed and tested a hydrogel for controlled lactate-responsive release of anti-tumor drug. In this specific example, the matrix is composed of a pH-responsive chitosan matrix, which encapsulates lactate oxidase and drug inside. The chitosan hydrogel swells with increased environmental lactate. Increased lactate concentration leads to enzymatic conversion of additional lactate into pyruvate and hydrogen peroxide (FIG. 3). Increased peroxide levels lead to increased availability of free protons (W), which in turn increases protonation of the chitosan network. Acting as a self-regulating valve system, this hydrogel matrix is able to release the drug in response to high lactate concentration.

Figure 4:
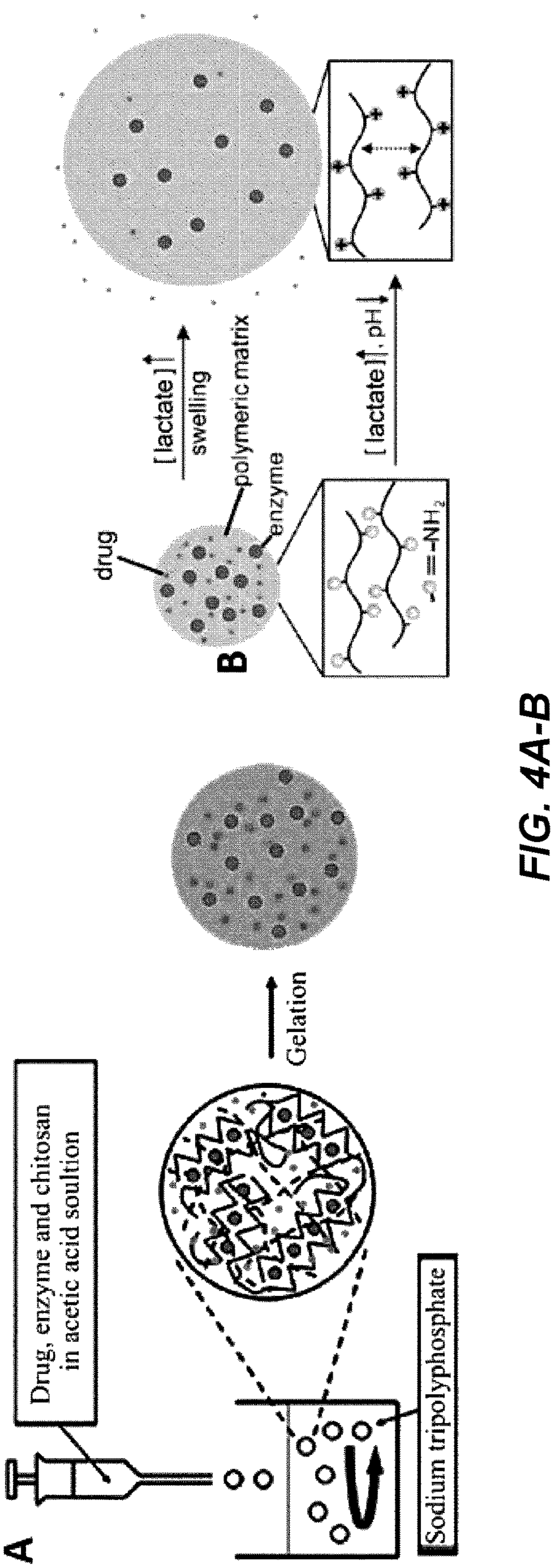
FIG. 4A-B Preparation of hydrogel for controlled lactate-responsive release.
Figure 5:
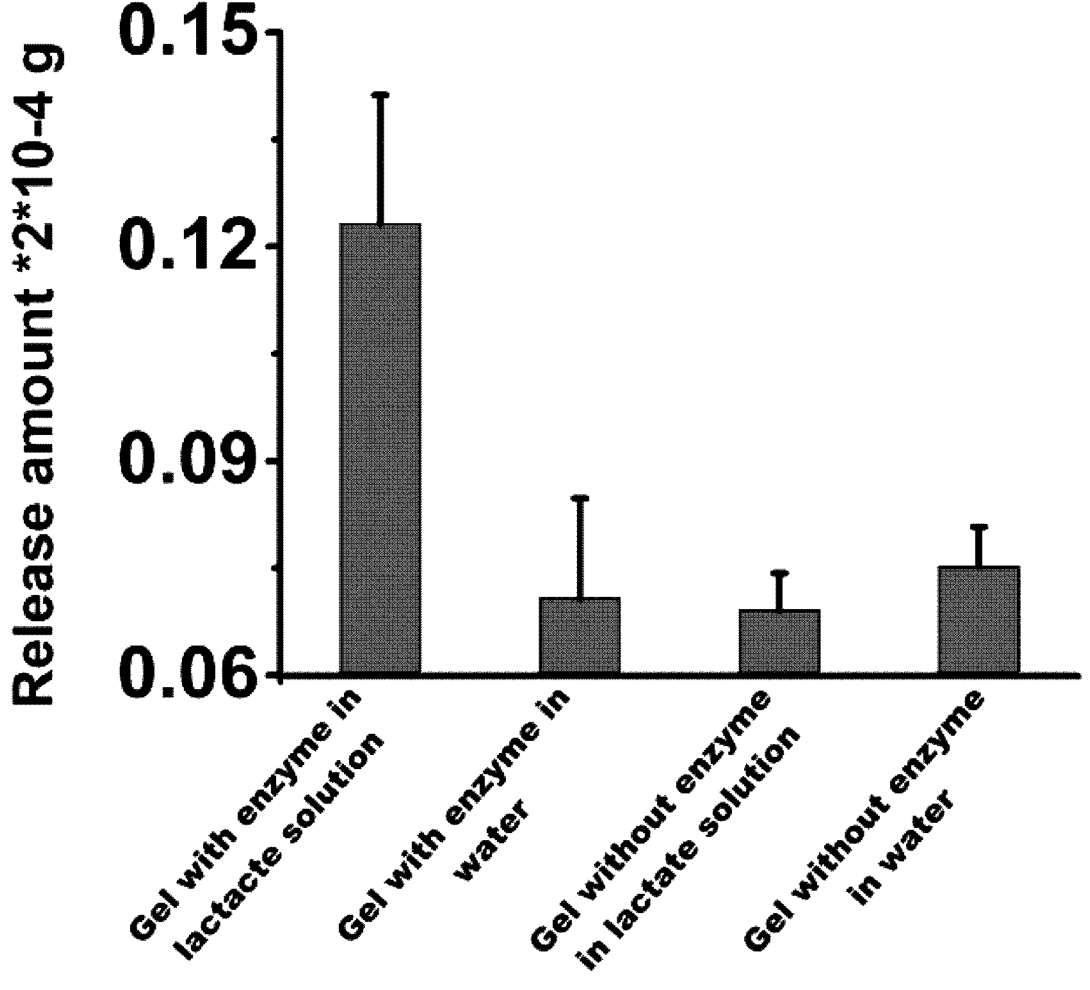
FIG. 5 Quantification of BSA release from engineered chitosan material in water or lactate solutions.
Figure 7:
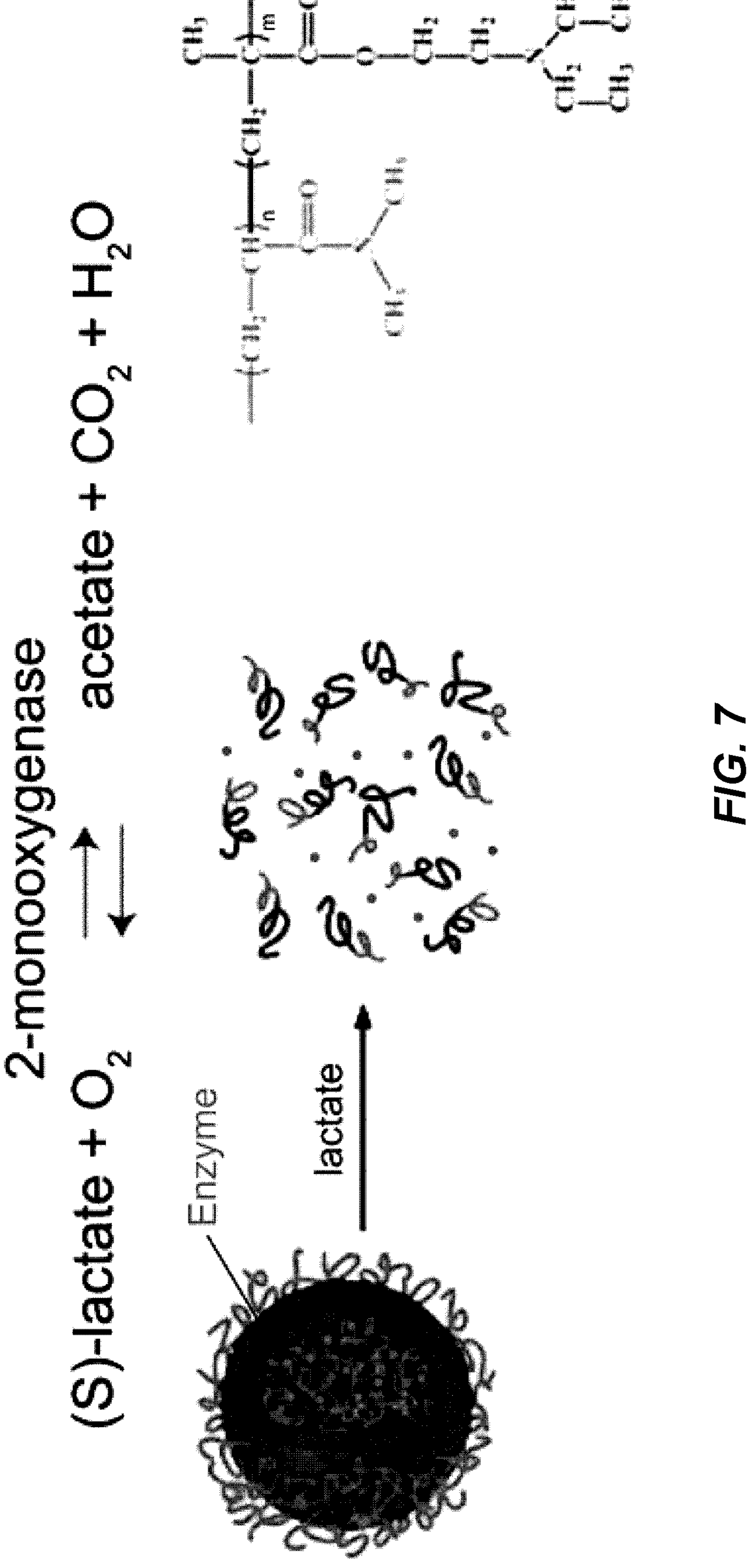
FIG. 7 Example of schematic illustration and the block copolymer structure of lactate-dissociable vesicle using $CO_2$-responsive polymers and the chemical reaction involving Lactate 2-monooxygenase.
Figure 8:
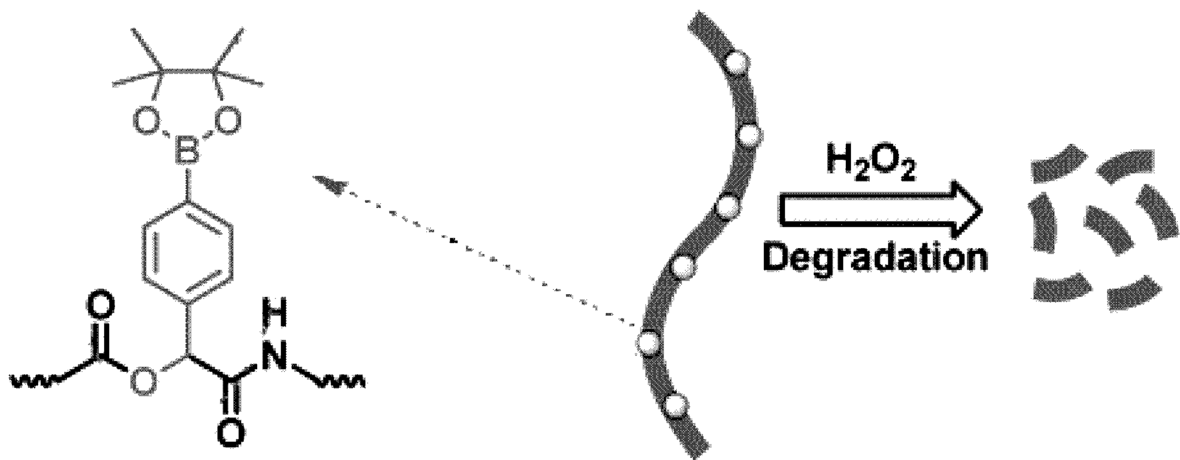
FIG. 8 Example of schematic illustration and the block copolymer structure of $H_2O_2$-dissociable polymer.

The hydrogel was prepared by dissolving chitosan in acetic acid solution with BSA (bovine serum albumin), BSA-alex488 and enzymes. The homogeneous mixture was transferred into a syringe and sprayed into sodium tripolyphosphate solution. The collected hydrogel particles were washed and separated evenly into two groups (FIG. 4). The prepared materials were exposed to water or 35 mM sodium lactate solution at 37° C. The supernatant was collected and the released BSA-alex488 was quantified by a fluorescence reader. A control experiment was performed using the same hydrogel in the absence of the enzymes. The inventors successfully detected significant levels of BSA-alex488 released from the hydrogel particles in the lactate-containing solution (FIG. 5).

Example 2

Similar to Example 1, the inventors can employ other pH-responsive polymer matrixes such as poly[(2-dimethylamino)ethyl methacrylate], poly[(2-diethylamino)ethyl methacrylate], poly[(2-diisopropylamino)ethyl methacrylate], poly(4-vinylpyridine) and poly(2-vinylpyridine). A large number of pH-responsive polymers can be designed using various electrolyte groups, and the pH-responsive polymers fall into two groups. One group includes polymers with acidic groups, and the other group includes polymers with basic groups.[7] When used in combination with lactate-related enzymes such as lactate oxidase or lactate dehydrogenase, the polymer matrix has the ability to respond to lactate indirectly, which leads to a physicochemical change of the polymer and achieves drug release.

Example 3

Lactate 2-monooxygenase was employed in a pH-responsive matrix using a different architecture to produce a lactate-responsive system. Lactate 2-monooxygenase produces $CO_2$, which may be employed as a signaling molecule for the stimuli-responsive polymers. These $CO_2$-responsive polymers can be built with different types of functional groups, including amidine, amine, or carboxyl group.[8,9] When lactate 2-monooxygenase produces $CO_2$, the polymer matrix will respond to lactate, leading to a physicochemical change of the polymer and ensuing drug release.

Example 4

The product of the enzymatic conversion of lactate can also be $H_2O_2$, which may serve as a target for the stimuli-responsive matrix. An $H_2O_2$-responsive platform can be built for multiple functions, including drug release, targeting imaging, diagnosis and treatment.[10,11] When combined with the lactate related enzymes such as Lactate oxidase, the matrix has the ability of respond to lactate. Based on the high reactivity of $MnO_2$ with $H_2O_2$, an $O_2$-generating hybrid nanoparticle can be employed for enhanced drug delivery.

Example 5

Figure 9:
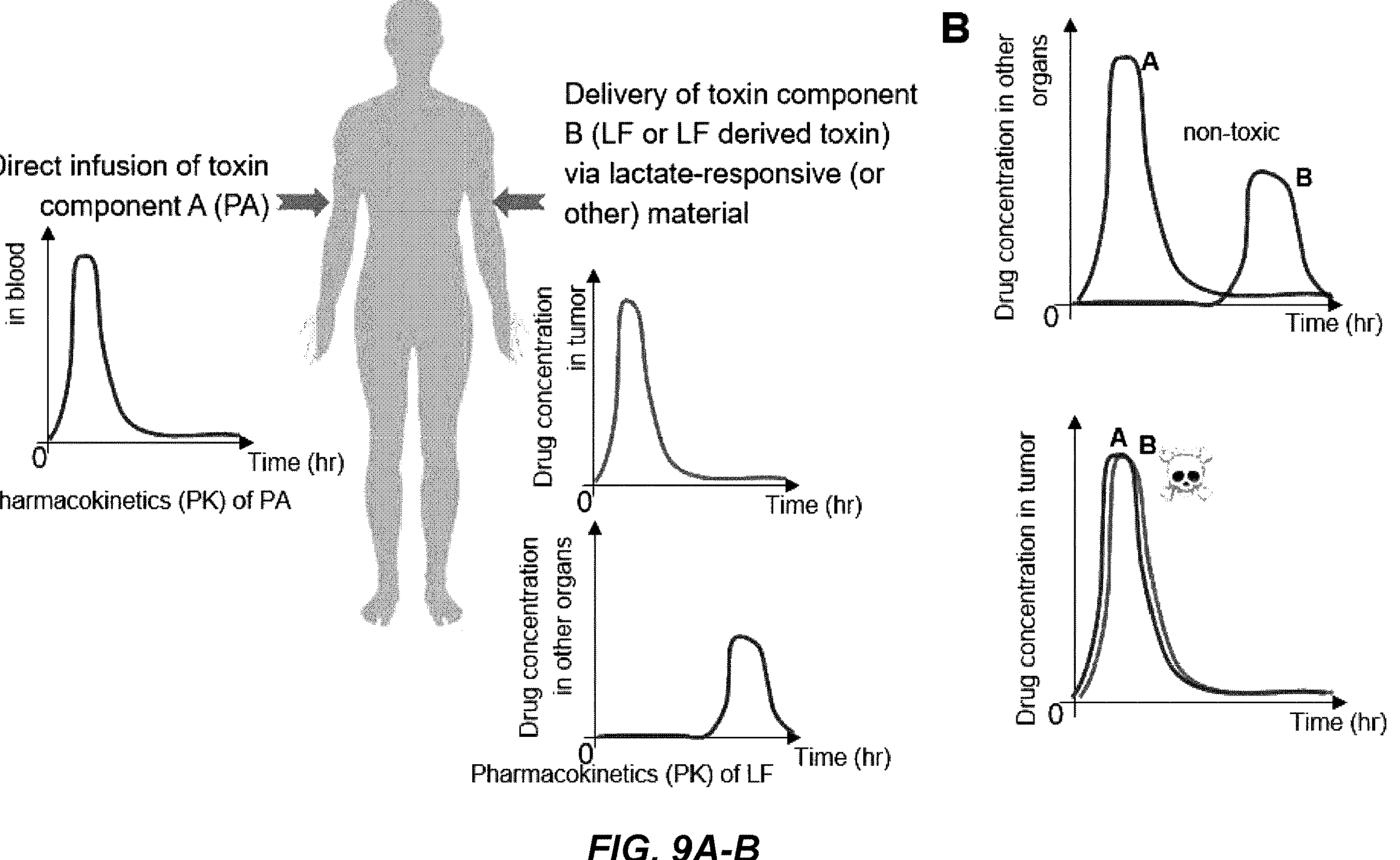
FIG. 9A-B Pharmacokinetics of toxin components A and B in normal and tumor environments. Particles will release content rapidly when exposed to high lactate concentration in tumor, but will keep the toxin inside the particles for much longer in normal tissue and organs (A). Toxic effects of drug are seen in tumor environment (bottom, B), and non-toxic effects are seen in normal, non-tumor environment (top, B).

In the experiment depicted in FIG. 9, the A component of the toxin (such as PA of anthrax toxin) will be directly infused to the blood. The free PA in blood will undergo rapid degradation and excretion in vivo (FIG. 9A, left graph). The B component of the toxin (such as LF, or modified LF, such as LFN-DTA) will be packaged in a tumor-responsive delivery particle, such as lactate-responsive particles. These particles will release the content rapidly when exposed to high lactate concentration in tumor (FIG. 9A, right-top graph), but will keep the toxin inside the particles for much longer in normal tissue and organs (FIG. 9A, right-bottom graph). Thus, with this design, the toxin component A and B can only bind in the tumor, and induce cytotoxicity in tumor cells (FIG. 9B, bottom graph). When the component B is released in normal tissues, the component A has already been degraded and excreted from the blood, and B component alone will not lead to significant side effect to the normal tissue (FIG. 9B, top graph). LFN=N-terminal region of Lethal Factor toxin. DTA=Diptheria Toxin A.

Example 6

Figure 10:
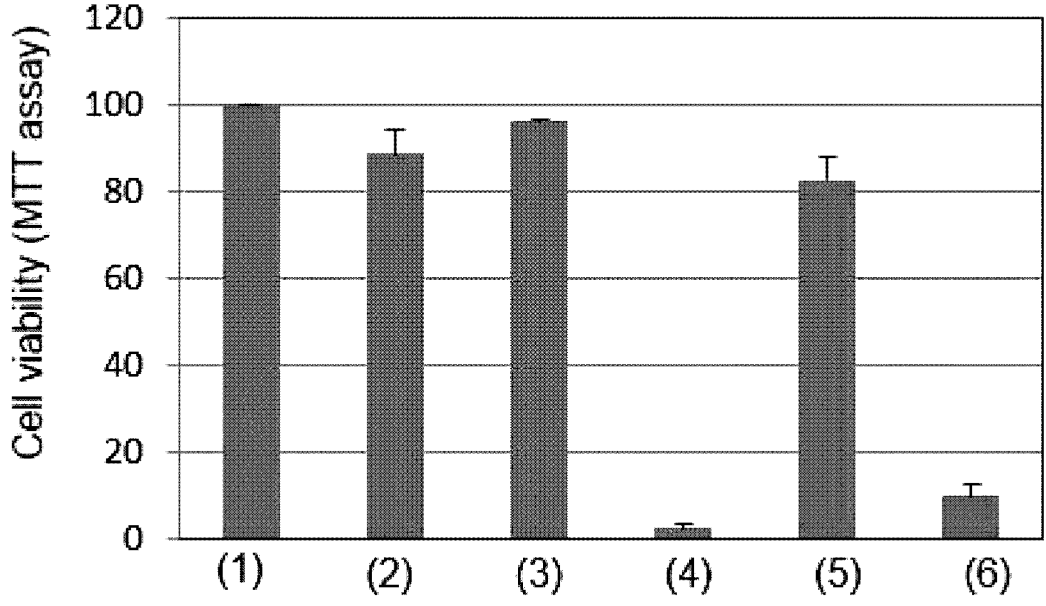
FIG. 10 AB toxin induced cytotoxicity in vitro. Quantification of cell viability (MTT assay) under different conditions: (1) control; (2) PA alone; (3) LFN-DTA alone; (4) PA+LFN-DTA; (5) free PA+LFN-DTA released from lactate-responsive particles in control solution; (6) free PA+LFN-DTA released from lactate-responsive particles in lactate solution. Cell viability was measured by MTT assay and normalized to the control cells (condition 1). LFN=N-terminal region of Lethal Factor toxin. DTA=Diptheria Toxin A.
Figure 11:
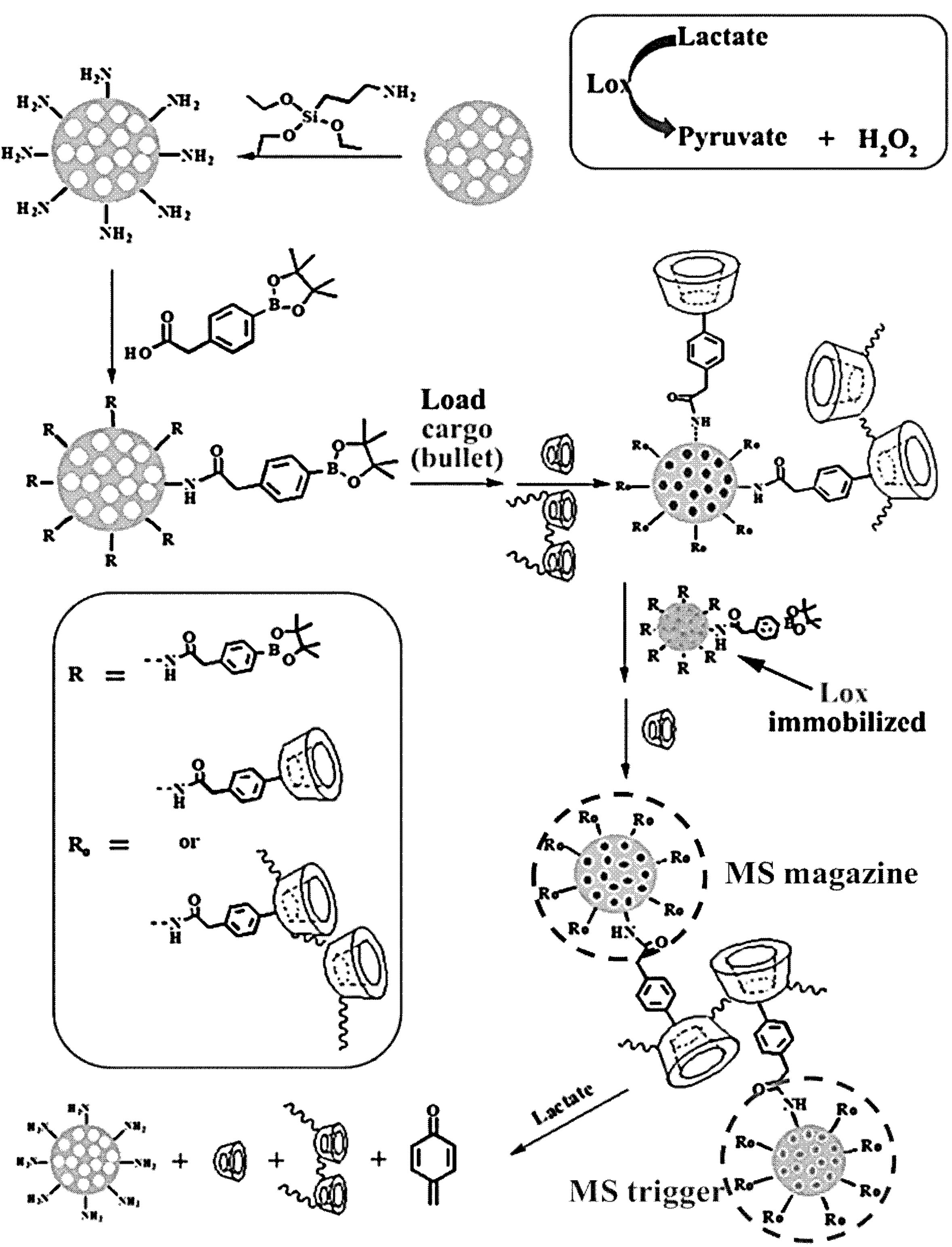
FIG. 11 Design and the performance of the lactate-responsive double-MS trigger-magazine system.
Figure 12:
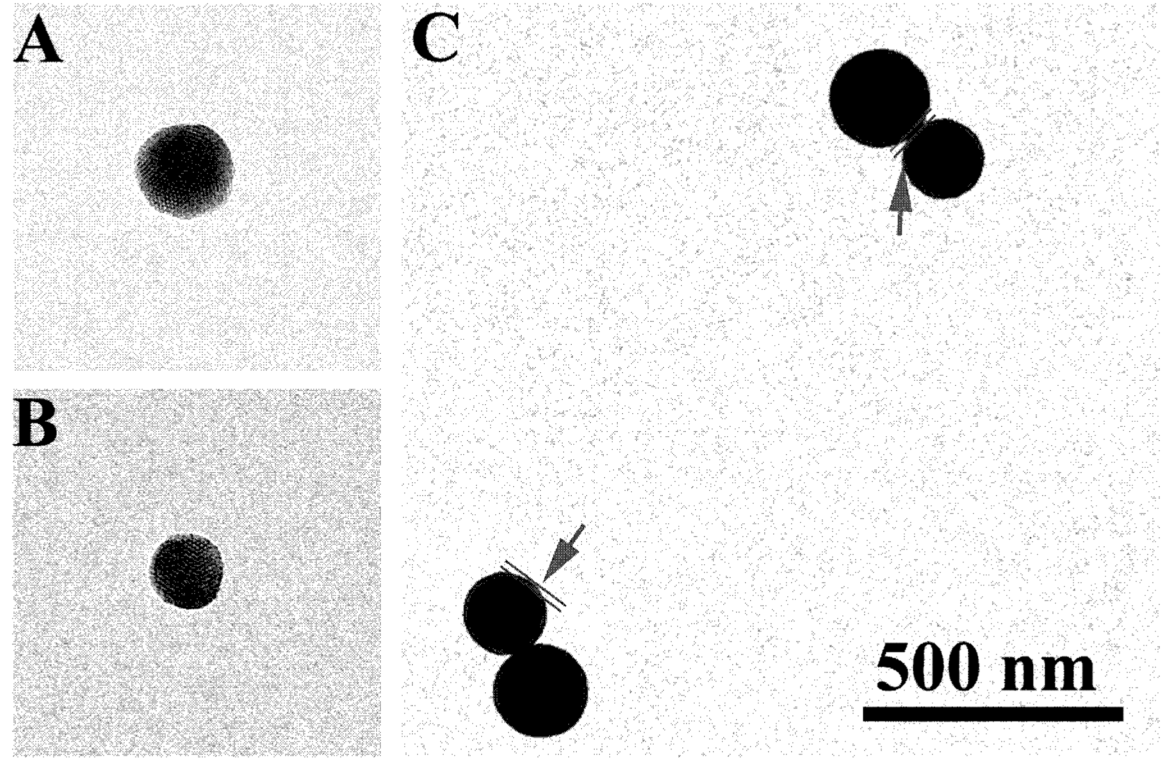
FIG. 12A-C Transmission electron microscopy (TEM) TEM results of the nanomaterials. Mesoporous nanosilica is used for the preparation of mesoporous nanosilica (MS)-magazine (A) and MS-trigger (B). Lactate-responsive double-MS trigger-magazine nanodevice (C). Arrow pointing to nanoparticle exterior is gating ensemble. Arrow pointing between nanoparticles is linker between MS-trigger and MS-magazine. Size of surface gating ensemble and linking between spherical MS-magazine is approximately 200 nm. Size of spherical MS-trigger is approximately 180 nm.

The graph depicted in FIG. 10 represents experimental results of AB toxin induced cytotoxicity in vitro. An MTT assay cell viability assay was performed under different conditions: (1) control; (2) protective antigen (PA) alone; (3) N-terminal region of lethal factor toxin in combination with Diptheria toxin A (LFN-DTA) alone; (4) protective antigen (PA)+LFN-DTA; (5) free PA+LFN-DTA released from lactate-responsive particles in control solution; (6) free PA+LFN-DTA released from lactate-responsive particles in lactate solution. Cell viability was normalized to the control cells, condition (1). Low cell viability was observed in the PA+LFN-DTA experiment (condition 4), resulting from co-administration of both A and B toxin components. Low cell viability was also observed in response to administration of free PA and LFN-DTA released from lactate-responsive particles in lactate solution (condition 6). The similar results observed in conditions 6 and 4 demonstrate that the lactate-responsive particles released their LFN-DTA payload in the high lactate environment (condition 6). Similar results are expected to be observed in a tumor microenvironment.

Example 7

The external surface of nanoparticles were functionalized with $H_2O_2$-sensitive selfimmolative arylboronate derivatives. The MS-magazine is first loaded with a selected "bullet" (i.e., payload drug), then capped by host-guest complexation with α-cyclodextrin (α-CD) and poly β-CD. Poly β-CD is also used as a linker for the MS-magazine and the MS-trigger. The MS-trigger is constructed by anchoring the enzyme Lactate oxidase (Lox) in the MS. Lox performs as: (i) a recognition agent for detecting the presence of lactate; (ii) a mediator agent, which produces hydrogen peroxide ($H_2O_2$) molecules and induces self-immolation reaction of arylboronate derivatives, resulting in uncapping of the MS pores and triggering the release of the bullet from the MS-magazine. After the MS-trigger detects lactate and sends the chemical messenger ($H_2O_2$), the MS-magazine receives the messenger then releases the payload drug as bullet.

Example 8

Figure 13:
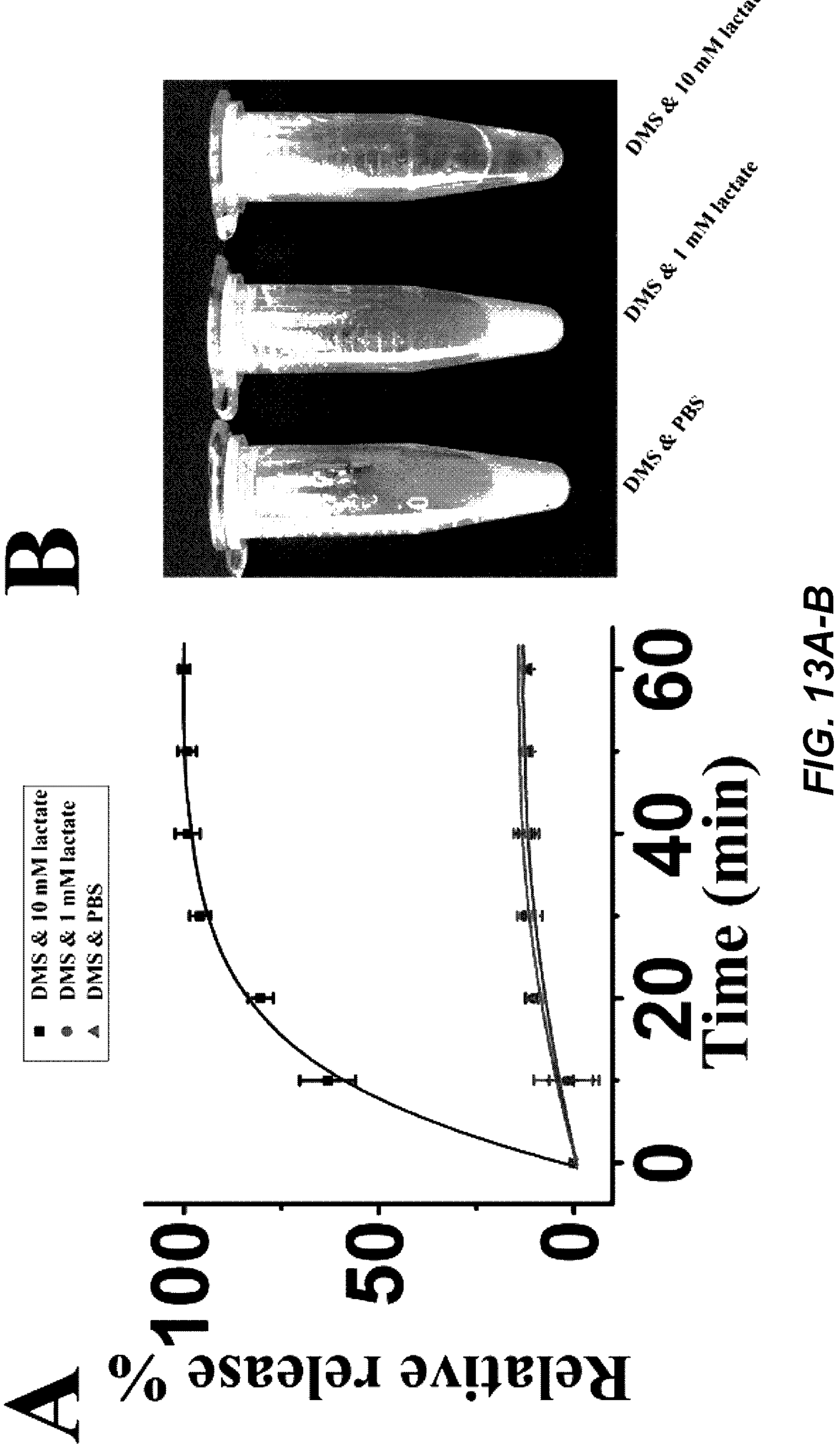
FIG. 13A-B In vitro release results for Doxorubicin (DOX)release (A). DMS status after cargo release for 1 hour (lactate-responsive double-MS trigger-magazine nanodevice loaded with DOX_(B).

In order to test the ability of the nanodevice to recognize lactate, release experiments were performed in which nanodevice DMS was brought to a concentration of 2.0 mg/mL in physiological buffer (PBS, pH 7.5) in the absence and presence of low and high concentration of lactate (1 mM and 10 mM). Samples were rotated at room temperature and, at scheduled times, aliquots were taken and centrifuged to remove nanoparticles. Cargo release was evaluated by measuring the fluorescence of the cargo. As shows in FIG. 13A, in the absence of lactate and the presence of low concentration lactate, the DMS is capped and cargo release was negligible. By contrast, a remarkable payload release was observed in the presence of high lactate concentration in less than one hour. The observed cargo delivery is ascribed to the recognition of lactate and its transformation to give $H_2O_2$ by the Lox enzyme. Subsequently, $H_2O_2$ acts as a chemical messenger sent by the enzymatic control unit (MS-trigger) to the MS-magazine. $H_2O_2$ induces the cleavage of the self-immolative arylboronate derivative, resulting in the payload delivered from the MS-magazine. By using DMS with a blank MS-magazine, in the absence of lactate and the presence of low concentration lactate, the DMS suspension appears as stable white colloid in 1 hour. By contrast, in the presence of high concentration lactate, the DMS precipitated to the bottom (FIG. 13B). This result can be attributed to the uncapping of the DMS and the aggregation of the uncapped silica nanoparticles.

Example 9

Figure 14:
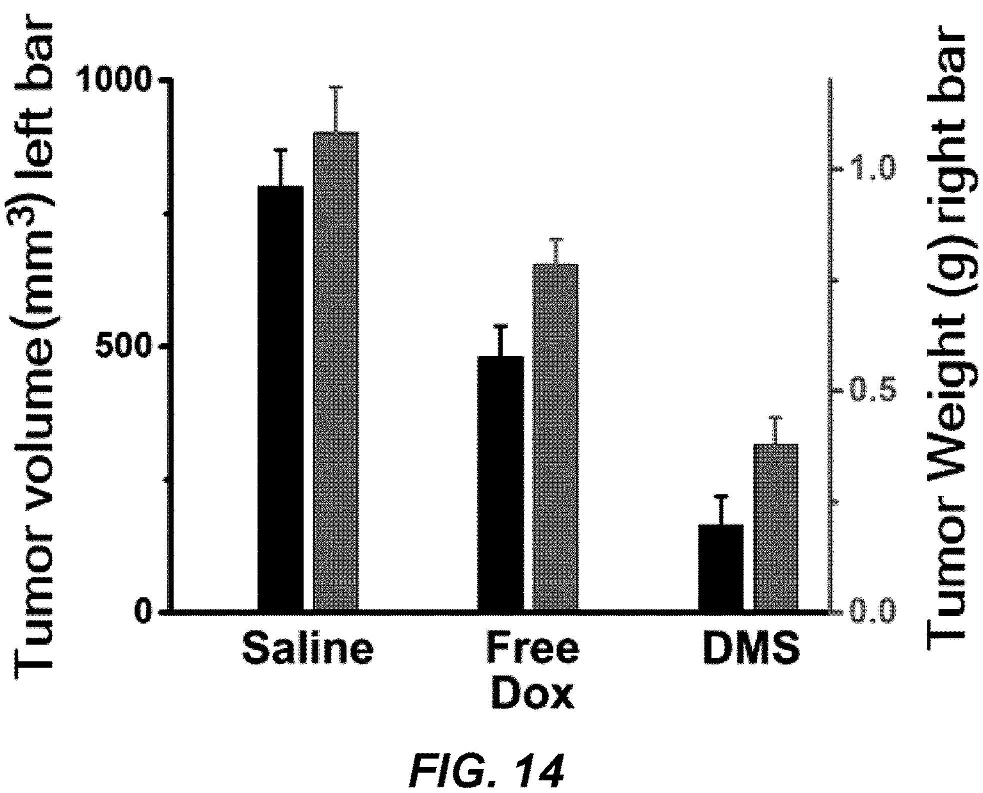
FIG. 14 Mice experiment result showed significant decrease of breast tumor size and weight in 3 days after DMS treatment.
Figure 15:
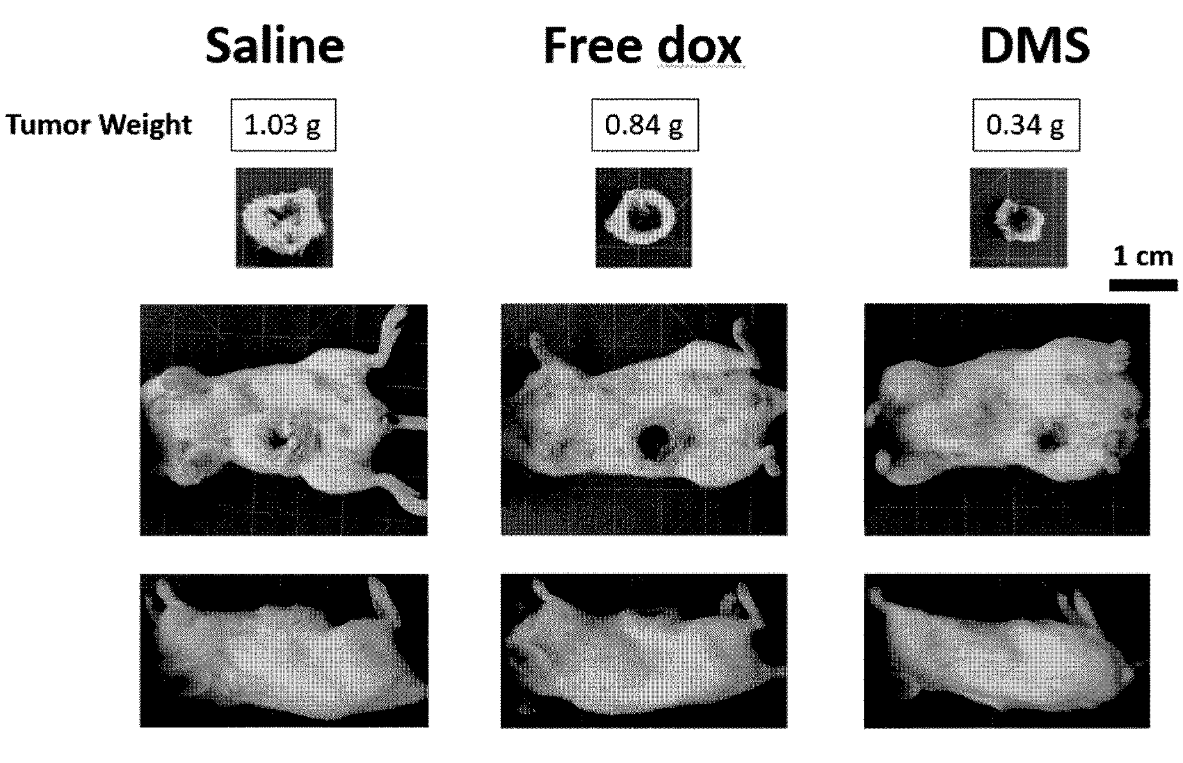
FIG. 15 Representative pictures at Day 3 after treatment confirmed the result of significant decrease of breast tumor size and weight in 3 days after DMS treatment.

Mice with breast tumors of approximately 1 cm were injected with DMS and monitored for three days. Two doses of 100 μl were injected in tail blood vein within 24 hours. DMS concentration in PBS was 40 mg/ml (approximately 70 μg Dox was loaded in 40 mg DMS). Free Dox control sample included a Dox concentration of 70 μg/ml in PBS. The result demonstrated significant decrease of breast tumor size and weight in 3 days after DMS treatment (FIG. 14). FIG. 15 shows representative pictures at day 3 after treatment. The tumor weights confirm that DMS treatment led to significant decreases in tumor size and weight after 3 days of treatment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and the publications referred to throughout the specification, to the extent that they provide exemplary procedural or other details supplementary to those set forth herein, are specifically incorporated herein by reference.

1. San-Millan, I. & Brooks, G. A. Reexamining cancer metabolism: lactate production for carcinogenesis could be the purpose and explanation of the Warburg Effect. Carcinogenesis 38, 119-133 (2017).
2. Hirschhaeuser, F., Sattler, U. G. & Mueller-Klieser, W. Lactate: a metabolic key player in cancer. Cancer research 71, 6921-6925 (2011).
3. Mura, S., Nicolas, J. & Couvreur, P. Stimuli-responsive nanocarriers for drug delivery. Nature materials 12, 991 (2013).
4. Lu, Y., Sun, W. & Gu, Z. Stimuli-responsive nanomaterials for therapeutic protein delivery. Journal of controlled release 194, 1-19 (2014).
5. Kanamala, M., Wilson, W. R., Yang, M., Palmer, B. D. & Wu, Z. Mechanisms and biomaterials in pH-responsive tumour targeted drug delivery: a review. Biomaterials 85, 152-167 (2016).
6. Marchiq, I. & Pouysségur, J. Hypoxia, cancer metabolism and the therapeutic benefit of targeting lactate/H+ symporters. Journal of Molecular Medicine 94, 155-171, doi:10.1007/s00109-015-1307-x (2016).
7. Kocak, G., Tuncer, C. & Bütün, V. pH-Responsive polymers. Polymer Chemistry 8, 144-176 (2017).
8. Lin, S. & Theato, P. CO2-Responsive Polymers. Macromolecular rapid communications 34, 1118-1133 (2013).
9. Yan, B., Han, D., Boissiẽre, O., Ayotte, P. & Zhao, Y. Manipulation of block copolymer vesicles using CO 2: dissociation or "breathing". Soft Matter 9, 2011-2016 (2013).
10. Yu, L., Chen, Y. & Chen, H. H2O2-responsive theranostic nanomedicine. Chinese Chemical Letters 28, 1841-1850 (2017).
11. Cui, Y., Zhang, M., Du, F.-S. & Li, Z.-C. Facile Synthesis of H2O2-Cleavable Poly (ester-amide) s by Passerini Multicomponent Polymerization. ACS Macro Letters 6, 11-15 (2016).
12. De Jong, W. H. et al. Particle size-dependent organ distribution of gold nanoparticles after intravenous administration. Biomaterials 29, 1912-1919, doi:10.1016/j.biomaterials.2007.12.037 (2008).
13. Huang, X. et al. The shape effect of mesoporous silica nanoparticles on biodistribution, clearance, and biocompatibility in vivo. ACS nano 5, 5390-5399, doi:10.1021/nn200365a (2011).
14. Minchin, R. Nanomedicine: sizing up targets with nanoparticles. Nature nanotechnology 3, 12-13, doi:10.1038/nnano.2007.433 (2008).
15. Semete, B. et al. In vivo evaluation of the biodistribution and safety of PLGA nanoparticles as drug delivery systems. Nanomedicine: nanotechnology, biology, and medicine 6, 662-671, doi:10.1016/j.nano.2010.02.002 (2010).
16. van der Zande, M. et al. Distribution, elimination, and toxicity of silver nanoparticles and silver ions in rats after 28-day oral exposure. ACS nano 6, 7427-7442, doi: 10.1021/nn302649p (2012).
17. Zhang, X. D. et al. Size-dependent in vivo toxicity of PEG-coated gold nanoparticles. International journal of nanomedicine 6, 2071-2081, doi:10.2147/IJN.S21657 (2011).
18. Ffrench-Constant, R. & Waterfield, N. An ABC guide to the bacterial toxin complexes. Advances in applied microbiology 58, 169-183 (2006).
19. Schiavo, G. & van der Goot, F. G. The bacterial toxin toolkit. Nat Rev Mol Cell Biol 2, 530-537, doi:10.1038/35080089 (2001).

The invention claimed is:

1. A lactate-triggered, benefit agent release composition comprising:

(a) a chemical-responsive matrix comprising a mesoporous silica nanoparticle (MSN) functionalized with an $H_2O_2$-sensitive arylboronate derivative linker that binds a cyclodextrin cap to the MSN surface;

(b) a lactate reacting enzyme immobilized on the surface of the MSN or on the surface of the cyclodextrin cap; and (c) a benefit agent provided within the MSN and retained therein by the cyclodextrin cap;

wherein the lactate reacting enzyme is capable of converting lactate into $H_2O_2$ and the $H_2O_2$ cleaves the $H_2O_2$-sensitive arylboronate derivative linker releasing the cyclodextrin cap from the MSN surface and enabling the benefit agent to escape from the MSN.

2. The lactate-triggered, benefit agent release composition of claim 1, wherein the lactate reacting enzyme is selected from the group consisting of lactate oxidase and lactate 2-monooxygenase.

3. The lactate-triggered, benefit agent release composition of claim 1, wherein the benefit agent is a therapeutic agent or a diagnostic agent.

4. The lactate-triggered, benefit agent release composition of claim 3, wherein the therapeutic agent is a small molecule, a peptide or polypeptide, a nucleic acid, nanoparticle, microparticle, ion, salt, bacteria, virus, live cells, or a radiopharmaceutical.

5. The lactate-triggered, benefit agent release composition of claim 3, wherein the therapeutic agent is a chemotherapeutic, an immunotherapeutic, a gene therapy agent, toxin, or a radiotherapeutic.

6. The lactate-triggered, benefit agent release composition of claim 1, further comprising a B component or a modified B component from an AB Toxin Complex, wherein the modified B component is at least 50, 60, 70, 80, 90%, or more homologous to a B component and comprises a region that interacts with an A component from the AB Toxin Complex.

7. The lactate-triggered, benefit agent release composition of claim 6, wherein the B component is Cholera toxin, Diptheria toxin, Pertussis toxin, *E. coli* heat-labile toxin LT, Shiga toxin, *Pseudomonas* exotoxin A, Botulinum, toxin, Tetanus toxin, Anthrax toxin LF, *Bortella pertussis* AC, *Bacillus anthracis* EF, or *Staphylococcus aureus* Exfoliatin B.

8. A method for delivering a benefit agent to a lactate target area of a subject to be treated, the method comprising:

providing a benefit agent release composition comprising a chemical-responsive matrix comprising a mesoporous silica nanoparticle (MSN) functionalized with an $H_2O_2$-sensitive arylboronate derivative linker that binds a cyclodextrin cap to the MSN surface, a lactate reacting enzyme immobilized on the surface of the MSN or on the surface of the cyclodextrin cap, and a benefit agent provided within the MSN and retained therein by the cyclodextrin;

wherein the lactate reacting enzyme converts lactate into $H_2O_2$ and the $H_2O_2$ cleaves the $H_2O_2$-sensitive arylboronate derivative linker releasing the cyclodextrin cap from the MSN surface and enabling the benefit agent to escape from the MSN when the benefit agent release composition is exposed to a lactate target area, wherein the lactate target area has a lactate concentration that is higher than ambient physiological lactate concentration.

9. The method of claim 8, wherein the release of the benefit agent targets a benefit agent release to an area comprising higher than ambient physiological lactate concentration.

10. The lactate-triggered, benefit agent release composition of claim 5, wherein the benefit agent is doxorubicin.

* * * * *